(12) United States Patent
Deutsch

(10) Patent No.: US 7,893,842 B2
(45) Date of Patent: Feb. 22, 2011

(54) SYSTEMS AND METHODS FOR MONITORING HEALTH CARE WORKERS AND PATIENTS

(76) Inventor: Richard Deutsch, 8 Bayview Ave., Islip, NY (US) 11751-4202

( * ) Notice: Subject to any disclaimer, the term of this patent is extended or adjusted under 35 U.S.C. 154(b) by 436 days.

(21) Appl. No.: 12/011,506

(22) Filed: Jan. 28, 2008

(65) Prior Publication Data

US 2009/0091458 A1     Apr. 9, 2009

Related U.S. Application Data

(60) Provisional application No. 60/960,621, filed on Oct. 5, 2007.

(51) Int. Cl.
*G08B 23/00* (2006.01)
(52) U.S. Cl. ............... 340/573.1; 340/539.13; 340/573.4; 340/691.6
(58) Field of Classification Search .......... 340/573.1, 340/573.4, 539.11–539.13, 539.23, 539.25, 340/691.3–691.6, 541, 567
See application file for complete search history.

(56) References Cited

U.S. PATENT DOCUMENTS

| | | | |
|---|---|---|---|
| 5,202,666 | A | 4/1993 | Knippscheer |
| 5,610,589 | A | 3/1997 | Evans et al. |
| 5,808,553 | A | 9/1998 | Cunningham |
| 5,812,059 | A | 9/1998 | Shaw et al. |
| 5,952,924 | A | 9/1999 | Evans et al. |
| 6,031,461 | A | 2/2000 | Lynn |
| 6,147,607 | A | 11/2000 | Lynn |
| 6,211,788 | B1 | 4/2001 | Lynn et al. |
| 6,236,317 | B1 | 5/2001 | Cohen et al. |
| 6,236,953 | B1 | 5/2001 | Segal |
| 6,278,372 | B1 | 8/2001 | Velasco |
| 6,727,818 | B1 | 4/2004 | Wildman et al. |
| 6,838,992 | B2 | 1/2005 | Tenarvitz |
| 6,882,278 | B2 | 4/2005 | Winings et al. |

(Continued)

OTHER PUBLICATIONS

International Search Report and Written Opinion of the International Searching Authority dated Mar. 10, 2009 and relating to International Application No. PCT/US 09/00444.

(Continued)

*Primary Examiner*—Thomas J Mullen
(74) *Attorney, Agent, or Firm*—Otterstedt, Ellenbogen & Kammer, LLP

(57) ABSTRACT

Systems and methods are provided for monitoring one or more patients to ensure compliance with required hygienic procedures and/or to ensure only authorized persons are allowed to attend to such patients. One system includes detectors that may be sequentially activated as a person approaches a patient. Activation of the detectors, in sequence, causes a signal to be transmitted by a controller. If the person is wearing a monitor and has complied with the required hygienic procedure, the monitor transmits a responsive signal to the controller that is encoded to indicate such compliance. If the person is either not wearing a monitor or the monitor does not transmit an appropriate responsive signal, the controller can provide a warning signal and cause a violation of protocol to be recorded. The system may include a portable sanitizer that is capable of functioning as a monitor. The systems and methods do not, however, require monitors worn by health care workers or other persons. Sensors may be associated with a hospital bed and/or a patient.

32 Claims, 17 Drawing Sheets

U.S. PATENT DOCUMENTS

| | | |
|---|---|---|
| 6,975,231 B2 | 12/2005 | Lane et al. |
| 6,987,451 B2 | 1/2006 | McKeown et al. |
| 7,015,816 B2 | 3/2006 | Wildman et al. |
| 7,612,666 B2 | 11/2009 | Badawy |
| 2003/0030562 A1* | 2/2003 | Lane et al. ............... 340/573.4 |
| 2003/0133614 A1 | 7/2003 | Robins et al. |
| 2006/0132316 A1 | 6/2006 | Wildman et al. |
| 2007/0080801 A1 | 4/2007 | Weismiller et al. |
| 2008/0246599 A1* | 10/2008 | Hufton et al. ............... 340/529 |

OTHER PUBLICATIONS

QTouch Sensor IC, 1999-2004, Quantum Research Group.

Low-Power SoC (System-on-Chip) with MCU, Memory, 2.4 GHz RF Transceiver, and USB Controller, undated, p. 1 of 241, Texas Instruments.

Salynn Boyles, More U.S. Deaths From MRSA Than AIDS, Oct. 16, 2007, WebMD Medical News.

* cited by examiner

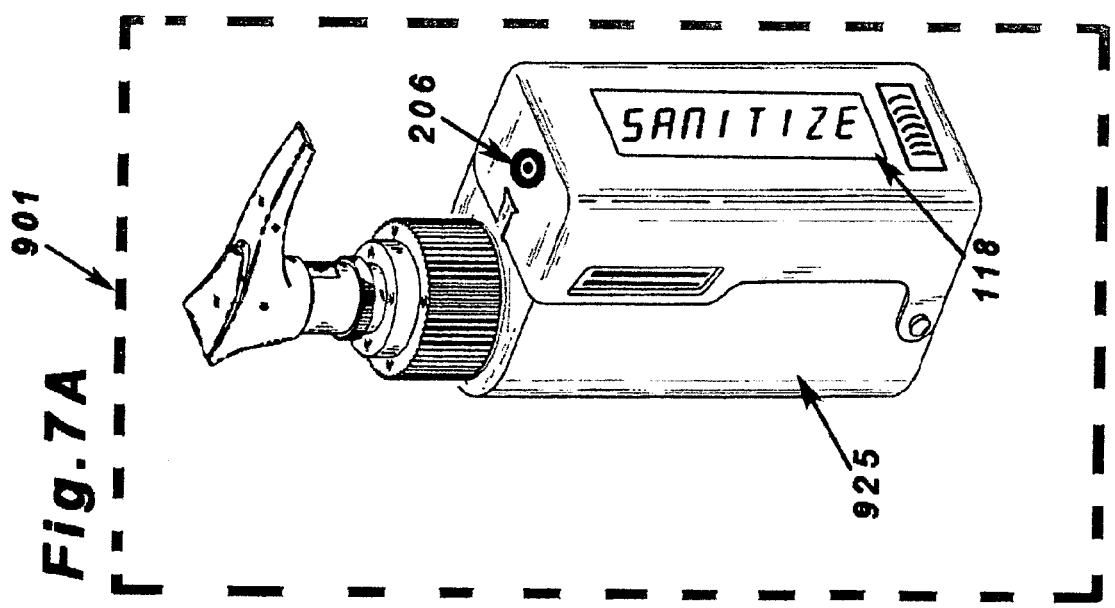
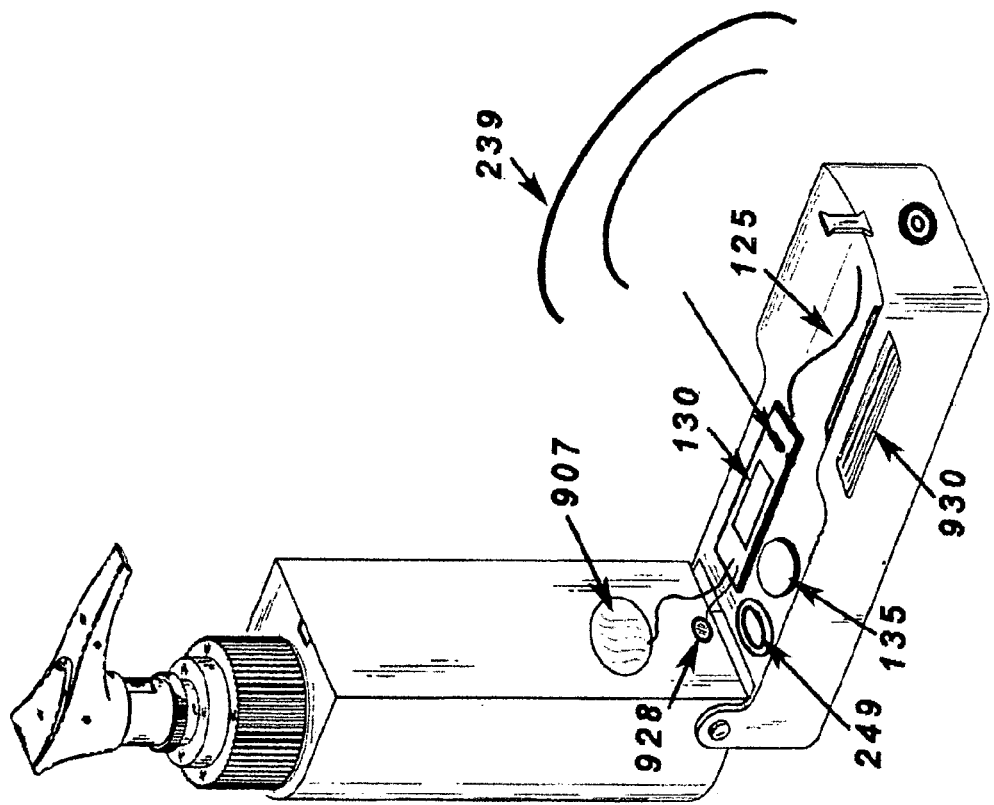

SYSTEMS AND METHODS FOR MONITORING HEALTH CARE WORKERS AND PATIENTS

BACKGROUND OF THE INVENTION

1. Field of the Invention

The field of the invention relates to systems and methods for monitoring health care workers to promote compliance with required hygienic practices and protect patients who may be contacted by such workers or other persons.

2. Brief Description of the Related Art

The Center for Disease Control, health care facilities and other institutions have recognized the need for promoting personal hygiene among workers. One of the most common practices by such institutions is to post signs in hallways and restrooms reminding workers that their hands must be washed. More sophisticated systems have been developed for monitoring the actions of workers. One such system includes badges worn by workers that are capable of transmitting or receiving information. As discussed in U.S. Pat. No. 6,236,317, workers are provided with badges that detect entry into an area that may be unsanitary and alert the workers to this fact. If a worker subsequently washes his hands or activates a disposable glove dispenser following such exposure, the alerting function of the badge is deactivated. If appropriate action is not taken by a worker, a violation is recorded by the badge or a system controller.

U.S. Pat. No. 6,882,278 describes another system that monitors compliance with recommended hand-washing practices. The system includes a hand-washing detector and an event detector such as a motion detector that detects an event such a person entering or leaving a room. A control unit determines whether a person has washed his hands within a predetermined time period before entering the room.

U.S. Pat. Nos. 6,727,818 and 6,975,231 disclose other systems for promoting hygienic practices. The first mentioned patent discloses a system that tracks the movements of health care workers throughout the facility and within a patient's room. The health care workers are provided with badges that transmit ID information to sensors located in the hallways and rooms of the facility, which in turn transmit location information to a master station. ID information is also transmitted to wash sink sensors to indicate whether the health care worker has washed his hands. If the health care worker enters a patient contact zone in the patient's room without having complied with the required hand washing procedure, an alert is provided by the health care worker's badge and/or other alerting devices located on the patient's bed or in the patient's room. A time delay may be employed before a warning alert is provided so that an alert is not triggered by a health care worker who is only briefly in the patient contact zone. U.S. Pat. No. 6,975,231 discloses a system employing sets of detectors located just outside and within a patient's room. These detectors are actuated sequentially as a person enters the room and the time between their actuation is monitored in determining whether a person has entered the room. A determination is made as to whether the person has washed his hands within a predetermined period of time, and a warning signal is generated if the hands have not been washed within the set period.

The benefits of signs reminding people to sanitize their hands are believed to be limited in effectiveness. Interactive systems that notify a person that he has not performed a required procedure are likely to result in better compliance, particularly if coupled with a system that makes a record of violations. It is important, however, to avoid "false alarms" that would cause a person to be notified of a compliance issue unnecessarily or record a violation where no issue of potential contamination is present. For example, a number of persons entering a hospital room do so for purposes other than treating a patient, and accordingly will not contact or even closely approach a patient. A system that signals hygienic warnings for such persons may tend to be ignored over time as too many warnings are issued during the course of a day. As patients are often capable of moving from their beds and in and out of their rooms, warnings due to such movements should either not be displayed or reflect the fact that they are patient-initiated. To the greatest possible extent, a system should display warnings only with respect to persons who actually come in close proximity or contact with a patient and have not complied with required hygienic practices before doing so. It is also important to detect unauthorized persons who may approach or come into contact with a patient regardless of whether they are wearing a badge or other type of transmitting/receiving apparatus.

SUMMARY OF THE INVENTION

The invention provides a method, a system, and system components that are designed to promote safe and hygienic practices within a hospital or other health care facility.

A method according to the invention includes detecting with a proximity sensor whether a person such as a health care worker (HCW) or other visitor is in close proximity to or in contact with a patient. The term "close proximity" may be defined as being within arms length of a patient support apparatus such as a hospital bed, a stretcher, a crib or the like upon which the patient is positioned. This may be a somewhat greater distance than the HCW or other visitor is from the patient himself. The method further includes determining whether the person has actuated a sanitizing device such as a hand sanitizer. A caution and/or warning signal, which can take many forms and cause any of a number of selected responses, is generated if the person is in close proximity or in contact with the patient and has not actuated the hand sanitizer. Depending on how the system is programmed, the caution or warning signals generated could cause the illumination of an indicator device or a text message to be displayed that reminds the person to wash his hands, advises the person and/or others that a violation has occurred, or instructs the person to vacate the patient care area. The sanitizing device is preferably associated with the particular patient, though the method may be designed so that the recent actuation of any sanitizing device in the facility will be sufficient to prevent the generation of a warning signal or the recording of a violation. The method also preferably includes a portable monitor to be worn or carried by the HCW that will provide personal identification information to the sanitizing device and/or other processors. Personal identification can alternatively be provided to the sanitizing device via RFID or biometric means such as fingerprint identification. Detection of a person in close proximity to the patient does not require the wearing of a monitor or other transmitting device. Accordingly, a person who is not wearing a monitor may be determined to be compliant or non-compliant reflecting whether or not he has washed his hands if he comes in close proximity to a patient. The system may provide a recording system, such as a video camera or digital imaging system or other means, for recording any non-compliant person who comes into close proximity to or in contact or near contact with a patient, whether such non-compliance is a result of not following required hygienic procedures and/or not wearing an appropriate monitor. Compliance of each individual HCW with the prescribed protocol can be monitored. In addition, violations of protocol with respect to a particular patient can also be monitored whether such violations are due to monitor-wearing health care workers and/or other persons who may not be wearing a monitor.

A second method in accordance with the invention includes detecting whether a person such as a HCW has come within a first distance of a patient and additionally detecting whether the person has come within a closer, second distance of the patient that is in close proximity to the patient. The method further includes generating a first selected message if the person has been detected sequentially coming within the first and second distances of the patient without having caused the actuation of a sanitizing device. The "first distance" is preferably selected such that the patient himself is unlikely to be detected in such a sequence while in the hospital bed and thereby generate false alarms or warning signals. This can be accomplished by appropriately positioning or shielding a detector. The first selected message can be a reminder to wash one's hands, a cautionary message, or warning that a violation has occurred. The message can be conveyed through text, sound, lights and/or other suitable means. The method may further include causing a message to be displayed upon detection of a person who has come within the first distance. The message may include information such as patient identification, special precautions and/or a reminder to wash one's hands, but will not ordinarily indicate a violation of procedure or provide an urgent warning.

A system for promoting hygienic practices includes a patient support apparatus such as a hospital bed or stretcher or the like and a proximity sensor operatively associated with the support apparatus. The sensor is associated with the support apparatus by being incorporated on or partially on the apparatus such that it can detect a person in close proximity thereto or possibly contacting the apparatus. An indicator is operatively associated with the sensor. In the preferred embodiment, the sensor is at least partially mounted to the apparatus. In a more specific and preferred embodiment, means are provided for generating a first signal only when the sensor has detected a person in close proximity to the patient support apparatus. A sanitizing device such as a soap dispenser, with or without a sink, is employed within the preferred system. Means are provided for generating a second signal when the sanitizing device is actuated. The second signal can be generated when, for example, soap is dispensed or some other activity associated with hand sanitizing occurs. The indicator device may be incorporated in a monitor worn by the person or patient and/or provided as a display located near the patient support apparatus. A processing assembly determines whether the second signal that results from actuation of the sanitizing device has been generated and causes the actuation of the indicator device if the second signal has not been generated and the proximity sensor has detected the presence of a person in close proximity to the patient support apparatus. If the system requires or permits use of a monitor worn or carried by the health care worker, the indicator device can be actuated should the worker or other person be detected in close proximity to the patient support apparatus without such a monitor. The system can be programmed, in certain circumstances, to detect whether the health care worker has used a glove and gown dispenser before coming into close proximity to a patient. Such dispensers may be provided to protect workers who need to treat patients suffering from infectious diseases, and can be considered sanitizing devices for the purposes of this application.

A system for monitoring patients is further provided that can be used to enhance patient safety and/or hygiene. The system includes first and second detectors. The second detector is capable of detecting whether a person has come in close proximity to or in contact with a patient support apparatus. A processing assembly is provided for determining whether the first and second detectors have been actuated. An indicator device is operatively associated with the processing assembly for generating a first message, which may be a warning signal or a message conveying other information, if the first and then the second detectors have been actuated in sequence, preferably within a preselected time period. The processing assembly may further include logic that causes the indicator device to generate a second message if a person has been detected sequentially by the second detector and then the first detector. Such detection may indicate that a patient has exited the bed and possibly the room. A selected message may also be generated when the first detector has been actuated. It is contemplated that the indicator device may be comprised of one or more elements such that messages or signals can be displayed in a variety of locations. For example, the first message resulting from actuation of the first and then the second detectors in sequence may be displayed in the patient's room. The second message may be displayed at a nursing station. A message can be generated in the form of words, sounds, lights and/or other means.

A patient monitoring system is also provided that requires contact or near contact with a patient or an article worn by, covering or otherwise contacting the patient by a HCW or other person in order for a signal to be generated. An indicator device is operatively associated with a proximity sensor in such a system. In a preferred embodiment, the system employs a charge transfer sensor that is worn by the patient or affixed to the patient's bed cover. The system may further include a sanitizing device and a processing assembly configured to determine whether the person contacting the patient or his clothing or covering has used the sanitizing device. A monitor may also be provided as part of the system, in which case the processing assembly is configured to determine the identity of and/or whether the person contacting the patient or an article in contact with the patient is wearing a monitor.

A sanitizing device that may be employed in conjunction with the systems and methods described above is further provided. The sanitizing device is associated with a particular patient or a particular area of a health care facility and is capable of communicating with a controller. Employment of such a sanitizing device helps ensure that a health care worker or other person has recently washed his or her hands or taken other appropriate action prior to contacting a particular patient or a patient within a particular area. The sanitizing device may be capable of receiving ID information from a monitor worn by a HCW and/or a biometric device that recognizes the HCW or other person using the sanitizing device. A portable sanitizing device is also provided that can perform the functions of a HCW monitor as well as being used for hand sanitation.

BRIEF DESCRIPTION OF THE DRAWINGS

FIG. 7A is a perspective view illustrating a sanitizer dispenser;

FIG. 7B is a perspective view thereof showing the sanitizer dispenser in an open position;

DETAILED DESCRIPTION OF THE PREFERRED EMBODIMENTS

A system for monitoring physical contact with or close proximity to a patient or medical equipment is provided. The system is capable of determining whether the person making such contact or near contact is in compliance with institutional hygienic rules, and particularly hand washing rules. It is further capable of determining whether a person who enters a patient's room presents a possible contamination threat irrespective of whether the person is wearing a monitoring device. A plurality of sensors is provided to detect the presence of persons who may approach a patient. The sensors are preferably capable of communication with a microcontroller. The system may be augmented with positional detection through the use of ZigBee 802.11, Bluetooth, GPS or other available technology. To promote compliance with institutional hand washing rules, violators of such rules may receive audible, visual and/or electro-stimulation warnings while records are made of their rule violations. While the invention is capable of modification, the specification which follows provides exemplary and preferred embodiments. It should be understood that the invention is not intended to be limited to the particular embodiments disclosed herein, but on the contrary is intended to cover all modifications, equivalents and alternatives falling within the spirit and scope of the invention.

Figure 1:
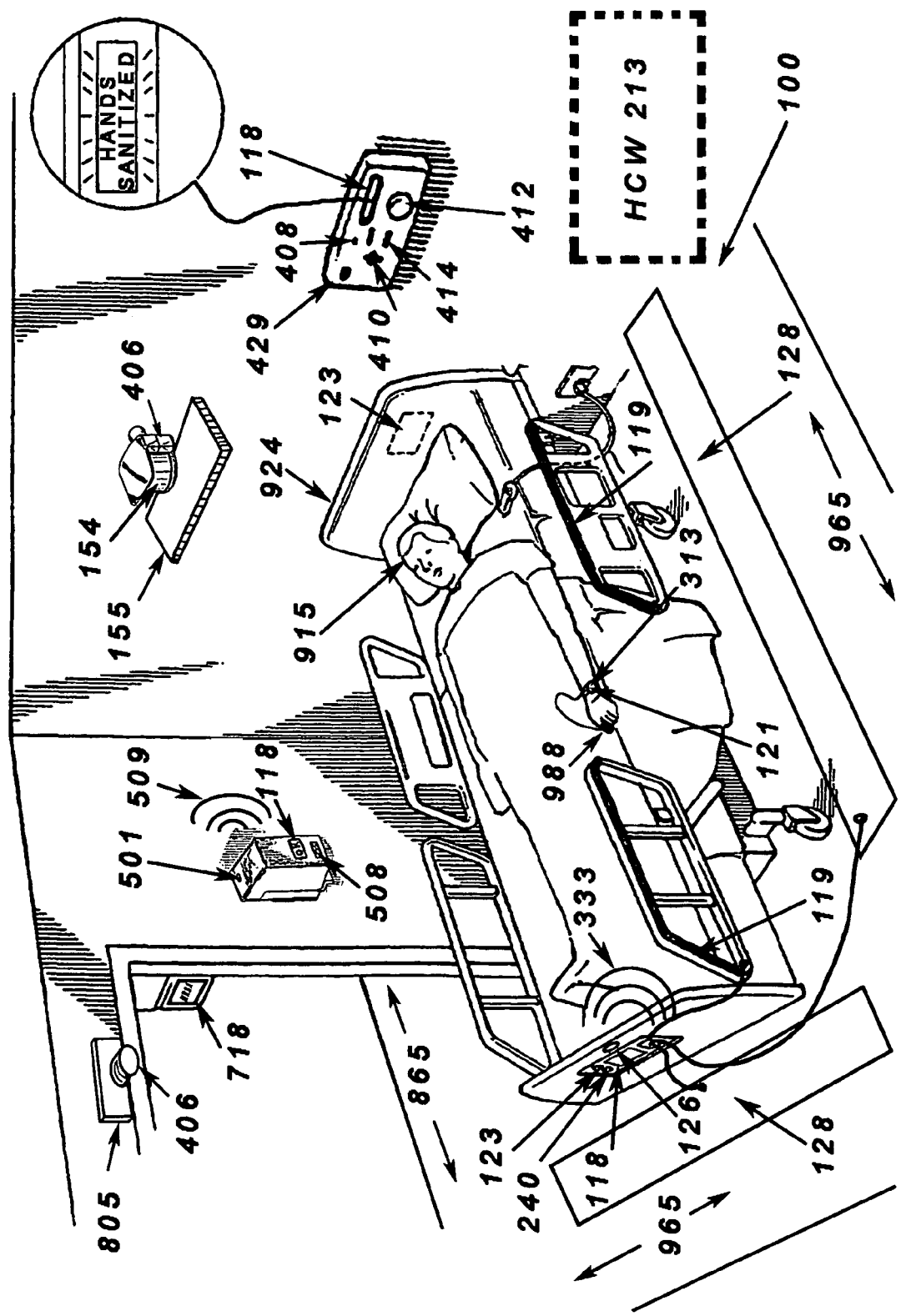
FIG. 1 is a perspective view showing a hospital room and a hygiene monitoring system in accordance with the invention.
Figure 16:
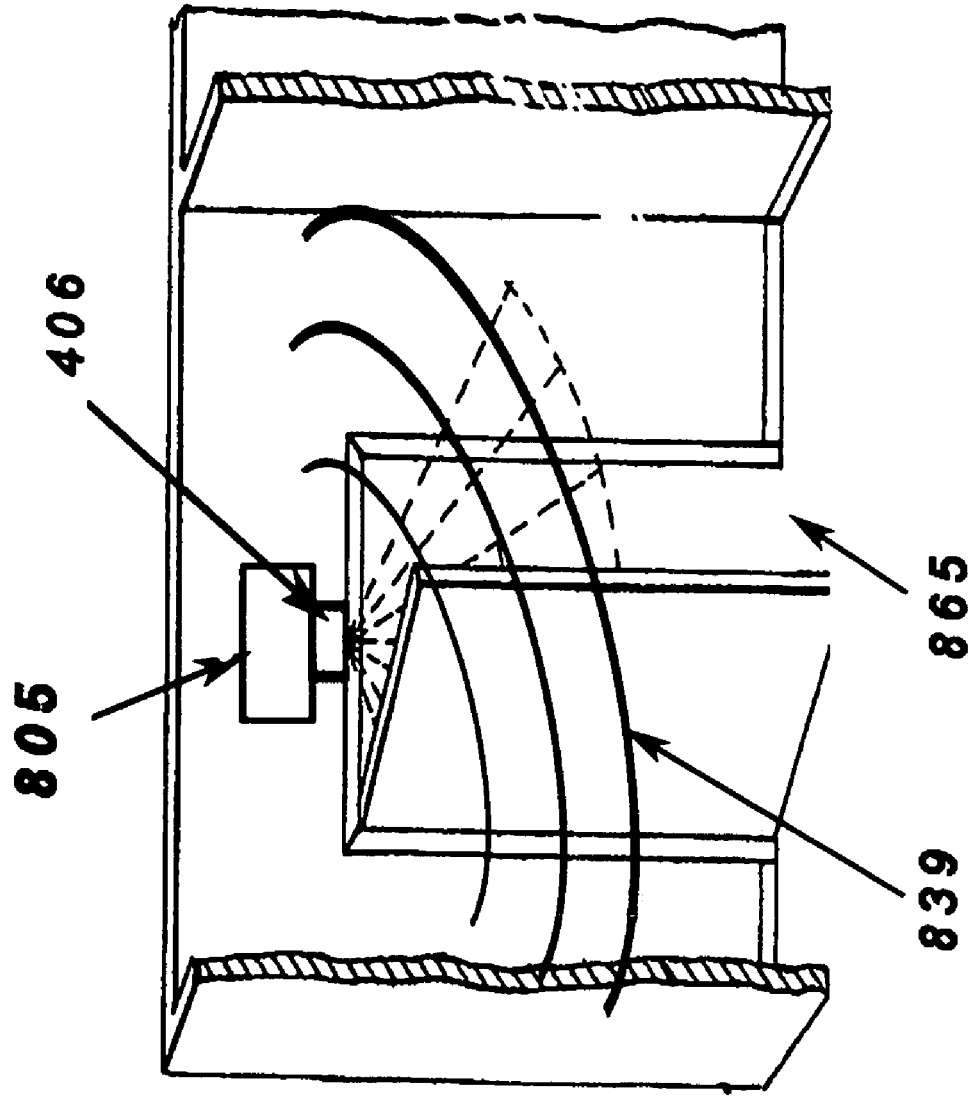
FIG. 16 is a perspective view of an entrance to a patient's room with a patient area motion detector above the entrance.

Referring to FIG. 1, a patient's room is shown as equipped with a system 100 for monitoring compliance with institutional hand washing rules. A patient 915 is shown within a hospital bed 924, both of which are located within a patient care area 965. It will be appreciated that the room may contain more than one patient and more than one patient care area. The room includes an entrance, and the room area within the entrance may be considered a contaminated area 865. As shown in FIGS. 1 and 16, a monitor 805 including a motion detector 406 is positioned just above the entrance. A second motion detector 406 is positioned above the bed. A shield 155 located beneath this second motion detector ensures that it will not detect ordinary movements of the patient while in the bed. A display device 718 is located just outside the room. A hand sanitizer 501 is shown within the patient's room, but additional or alternative sanitizers may be located within the patient's bathroom or in another suitable location. The hand sanitizer includes a sensor 508 and a transmitter capable of generating a signal 509. It further includes an annunciator 118, which may be in the form of an LCD display. The hand sanitizer shown is a "bag-in-box" type dispenser that receives a bladder filled with soap or other sanitizing agent.

Figure 5:
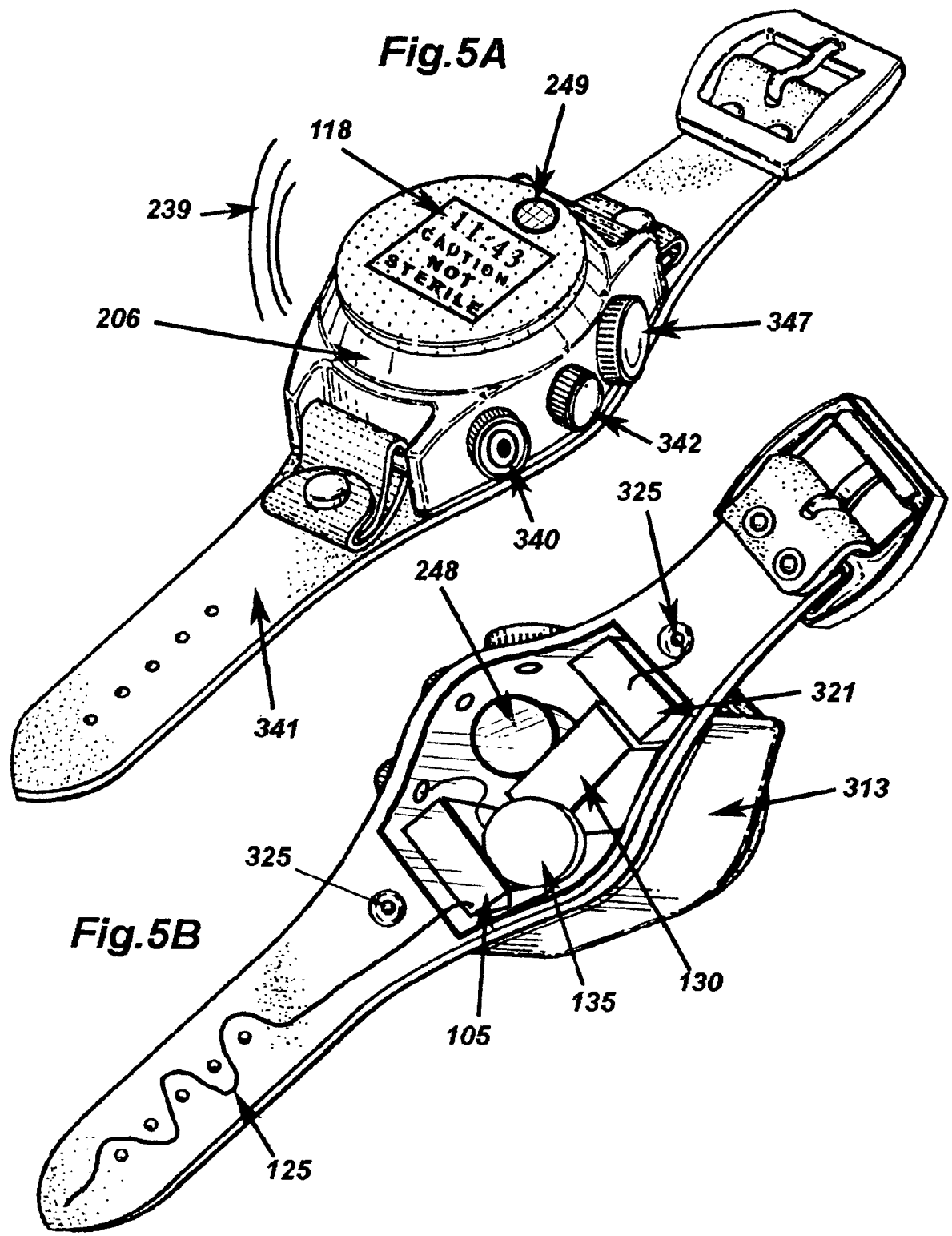
FIG. 5A is a top perspective view of a monitor adapted to be worn by a patient.
FIG. 5B is a bottom perspective view thereof.

The hospital room is equipped with a system of proximity sensors. These sensors are employed in combination with the motion detector(s) in the room to determine the presence and proximity of a health care worker to the patient (or the bed or other equipment) in one or more increments of increasing or decreasing proximity. One or more first proximity sensors 128 are located at the periphery of the patient care area 965 on the floor, which is in proximity to the bed 924. These sensors may be pressure sensors, charge transfer sensors, piezoresistive sensing floor strips, and/or infrared detectors mounted to a curtain rail that detect when a person is standing near the patient. Second proximity sensors 119, which may be charge transfer detectors, infrared sensors or other suitable detectors, are associated with the patient bed and preferably located on one or more of the bed rails. Depending on the type of sensor employed, it may be located entirely or just partially on the bed rail or other portion of the bed. The sensor(s) 119 are preferably located and/or directed where a patient in bed will be unlikely to be detected by them while a person standing next to, leaning over and/or contacting the bed will be detected. If used in conjunction with the first proximity sensors 128 as shown, they will preferably detect a person who moves or extends an arm beyond the first proximity sensors 128 or who contacts the rail. This allows the system 100 to distinguish between degrees of proximity to a patient if programmed to do so. The proximity detectors may alternatively provide redundancy, ensuring that a health care worker will indeed be detected by at least one of the detectors. A third proximity sensor 321 associated with the patient, shown in FIG. 5B, is preferably incorporated in a monitor 313 worn by the patient, though it could be located elsewhere. This sensor is preferably capable of detecting contact with a patient or an article worn by the patient or in contact with the patient, as described hereafter. The proximity sensors are all preferably designed to have limited range and/or direction so that a person must be within the patient care area 965 or even closer to the patient before being detected by any of them. Charge transfer sensors, as may be used for detecting patient or bed contact or near contact, typically have very limited range. The limited range and/or direction of all proximity sensors 128, 119, 321 allows the system to operate effectively in rooms having multiple patient care areas without interfering with health care workers who do not enter the patient care area 965 or contact the patient. It will be appreciated that the different proximity sensors may have different ranges as deemed appropriate.

Figure 2:
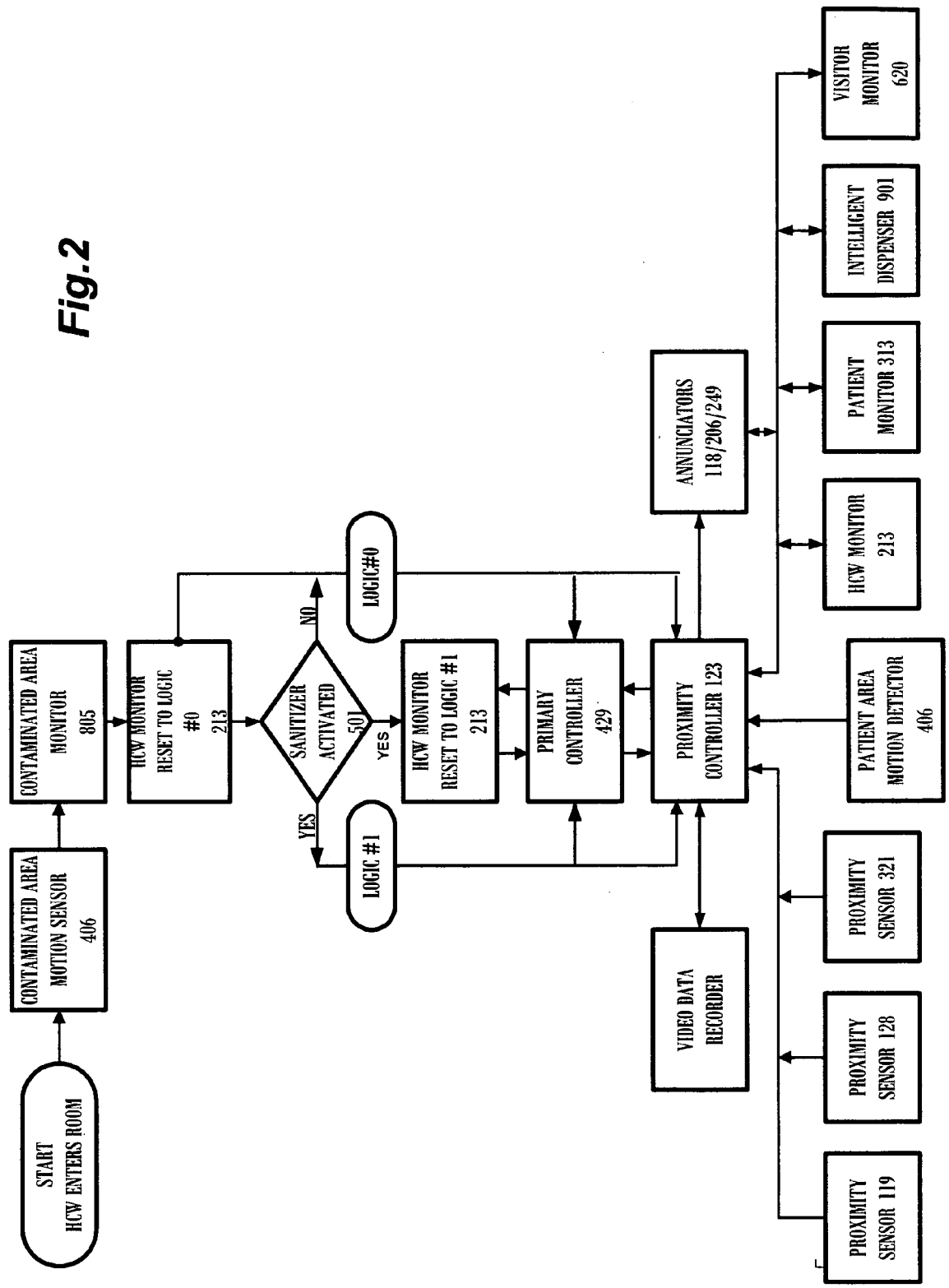
FIG. 2 is a flow diagram of a hygiene monitoring system.

A primary controller 429 is provided that is capable of communicating with one or more of the annunciators 118. While shown as a separate unit, the primary controller may be incorporated within the sanitizer 501. A light detector 408 may be incorporated in the controller housing. The controller housing may further be provided with a display control 410, a message select control 412, and a power switch 414. A proximity controller 123 is provided for receiving transmissions from the proximity sensors and possibly the signal 509 from the hand sanitizer 501. It may further store information relating to the patient and cause the display of such information on one or more of the annunciators. The proximity controller is also capable of transmitting information to the primary controller 429, preferably wirelessly. The proximity controller 123 is shown as incorporated on the footboard of the patient's bed, but may be located on the headboard, as shown in broken lines, or elsewhere in the room. A monitor 213 adapted to be worn by a health care worker is preferably capable of two-way communication, and can communicate with the proximity controller. FIG. 2 schematically illustrates the basic components of the monitoring system and the manner in which they communicate with each other.

Figure 4:
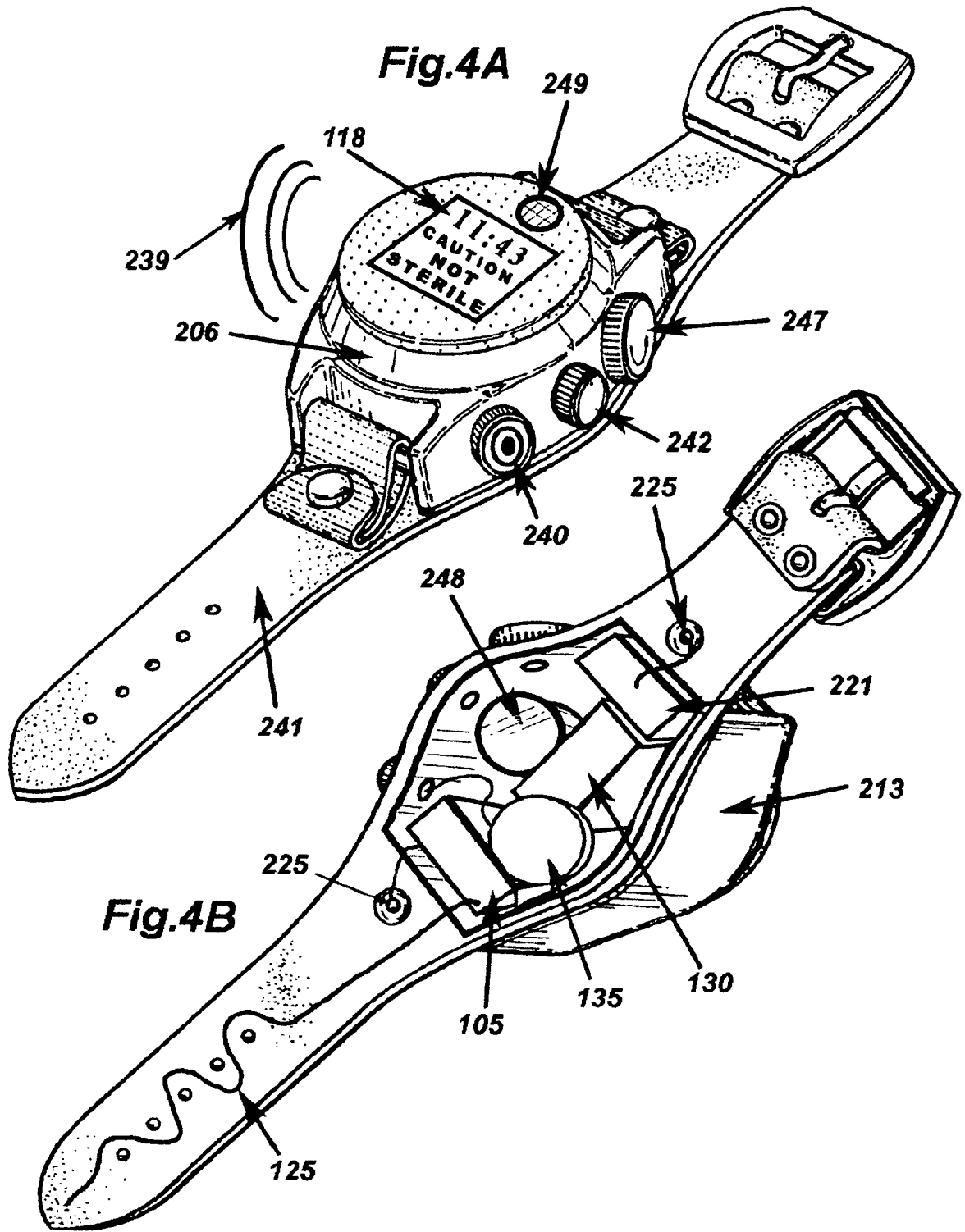
FIG. 4A is a top perspective view of a monitor adapted to be worn by a health care worker.
FIG. 4B is a bottom perspective view thereof.
Figure 11:
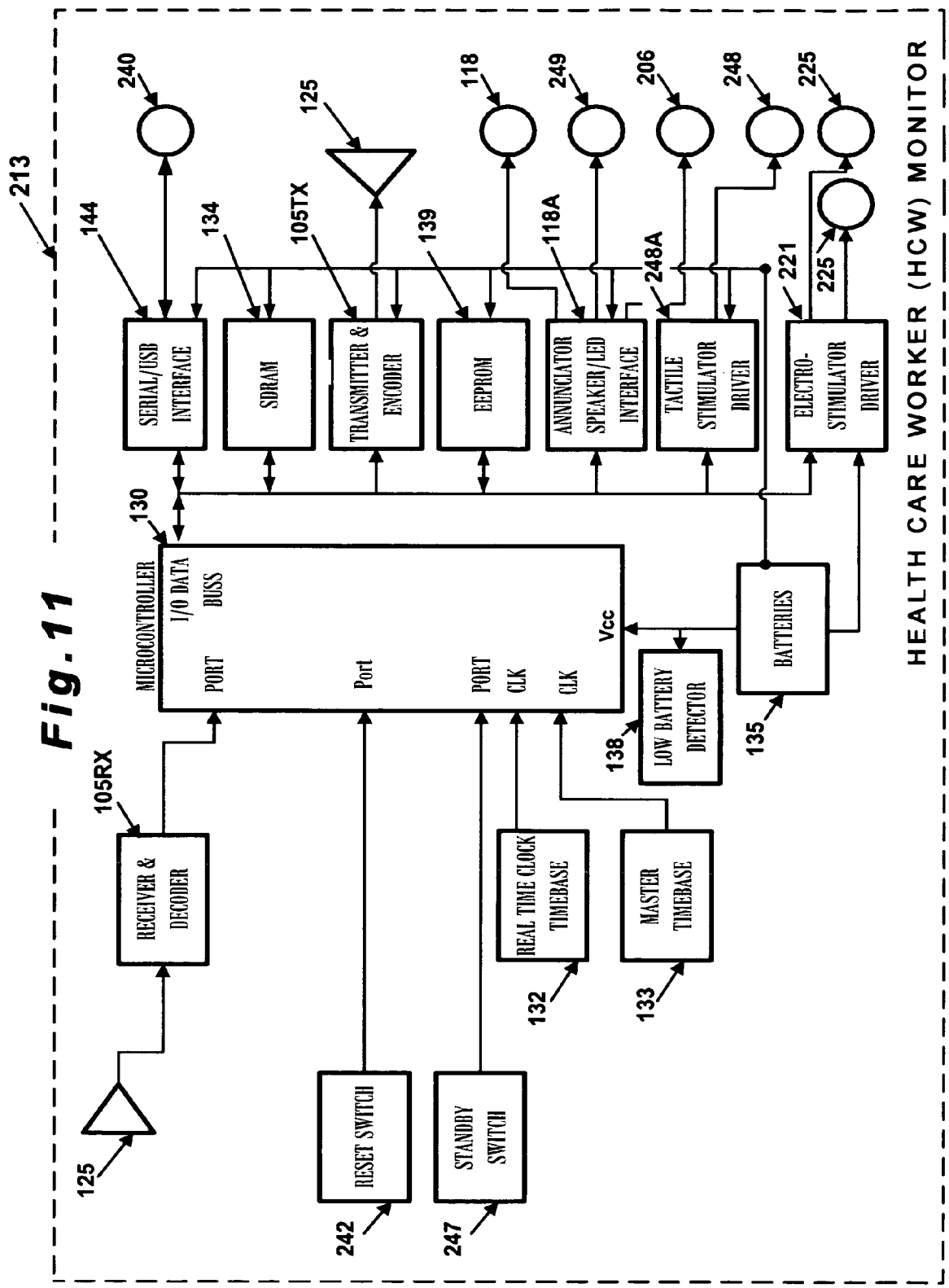
FIG. 11 is a diagrammatic illustration of the monitor shown in FIGS. 4A and 4B.

FIGS. 4A, 4B and 11 provide further details of the monitor 213 intended to be worn by health care workers using a wrist strap 241. The monitor includes a first annunciator 118 connected to an interface 118A, the annunciator being an LCD display capable of displaying alphanumeric characters on the top surface of the monitor housing. Information relating to rule compliance may be provided on this annunciator. An LED display 206 and a speaker 249 are also provided. The monitor is capable of transmitting a coded signal 239 to the proximity controller 123 through the use of a transmitting assembly 105. A standby switch 247 is provided for causing the monitoring system to enter a standby mode, which is intended for emergency situations. A reset switch 242 is also provided. Information may be transmitted wirelessly by means of an antenna 125 and associated transmitter and encoder 105TX or downloaded from the monitor via a USB connector 240 and associated USB data port 144. In addition to the displays, various alternatives are contemplated for alerting the health care worker in the event it is determined that the worker is not in compliance with the institution's hand washing protocol. A tactile stimulator 248, such as a vibrating mechanism, may be incorporated within the monitor housing and coupled to a driver 248A. Electro-stimulators 225 and an associated driver 221 capable of generating a mild electrical shock to the health care worker may also be provided. The monitor 213 includes a microcontroller 130 that is operated by one or more batteries 135. A low battery detector 138 may be provided for causing one of the displays to alert the user in the event the battery requires changing. The CPU (microcontroller 130) is employed for executing stored instructions. An EEPROM memory 139 stores instructions which can be retrieved and executed by the microcontroller 130. An SDRAM stores certain information that must be retained if the power source is interrupted, such as the nature of violations and the violator's ID. The master timebase 133 provides machine cycles for the microcontroller 130 and watchdog timers. A real time clock 132 provides time stamp information to the microcontroller 130 for documenting health care worker actions and/or violations.

Figure 10:
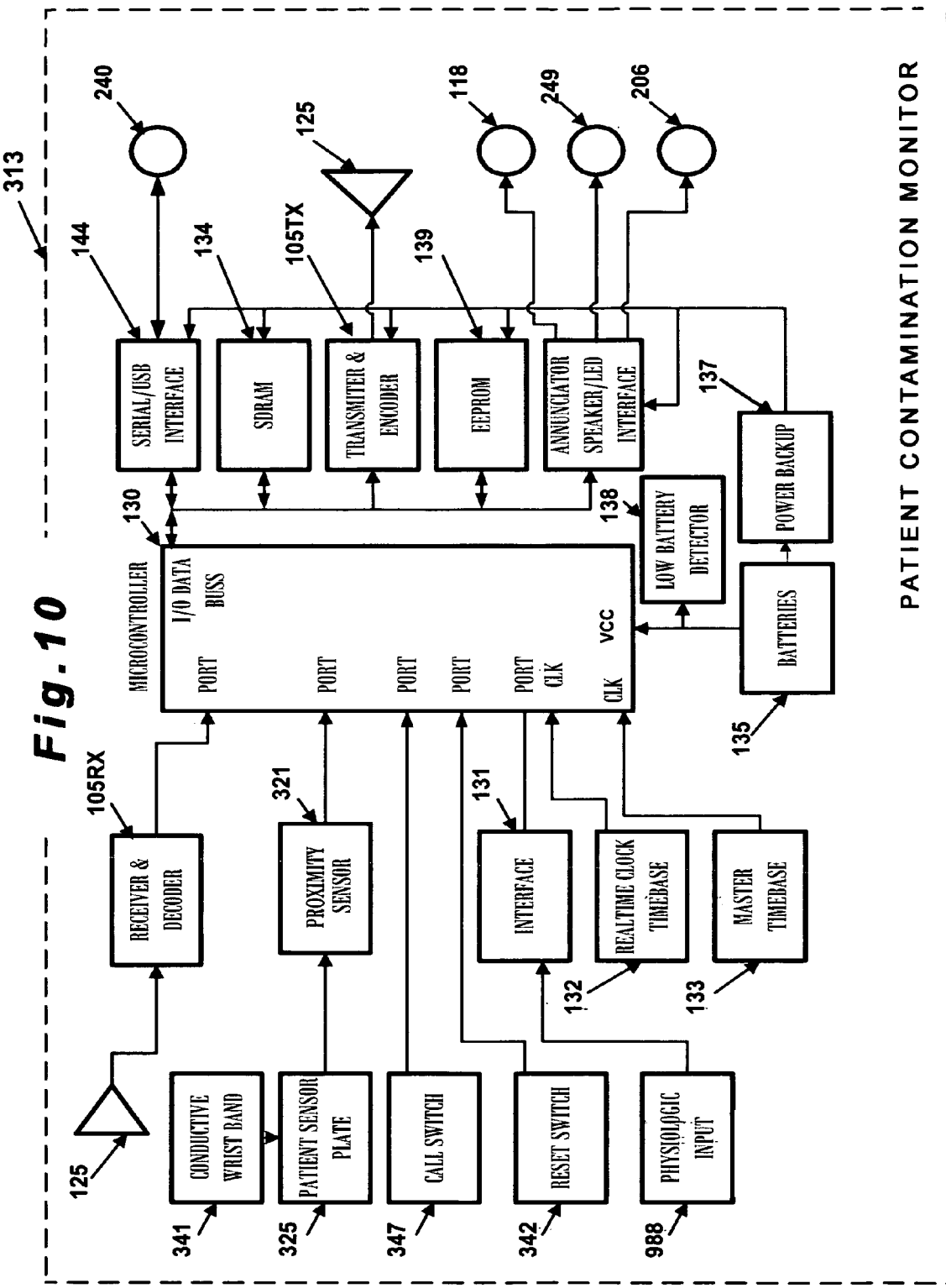
FIG. 10 is a diagrammatic illustration of the monitor shown in FIGS. 5A and 5B.

FIGS. 5A and 5B provide two views of the patient monitor 313, parts of which are illustrated schematically. FIG. 10 is a schematic diagram of this monitor 313, and includes additional details. The patient monitor 313 includes a number of components found in the health care worker monitor 213 which have been described above. The top surface of the monitor 313 includes an LCD display 118 capable of displaying alphanumeric characters and an LED display 206 which may be an LED. The monitor housing is secured to a wrist strap 341. The patient monitor 313 is pre-programmed with the associated patient's name and pertinent medical data. A proximity sensor 321 is contained therein and includes a pair of electrical contact pins 325. Upon physical contact by another person with the patient or an electrode associated with the sensor 321, a signal is directed to the proximity controller 123. The sensor 321 and/or electrode(s) associated with the proximity sensor may be incorporated on the patient monitor 313, clothing worn by the patient, or a sheet or cover for the patient. All detectors and proximity sensors employed in the system may be sensor assemblies including integrated circuits providing noise filtration and/or sensitivity adjustments. Other features of the patient monitor 313 include a call switch 347 to allow the patient to send a signal to a nursing station or elsewhere, a reset switch 342 and a power backup 137. The patient monitor may further comprise a physiological monitoring device, such as a pulse-oximeter 988, operatively associated therewith.

Figure 8:
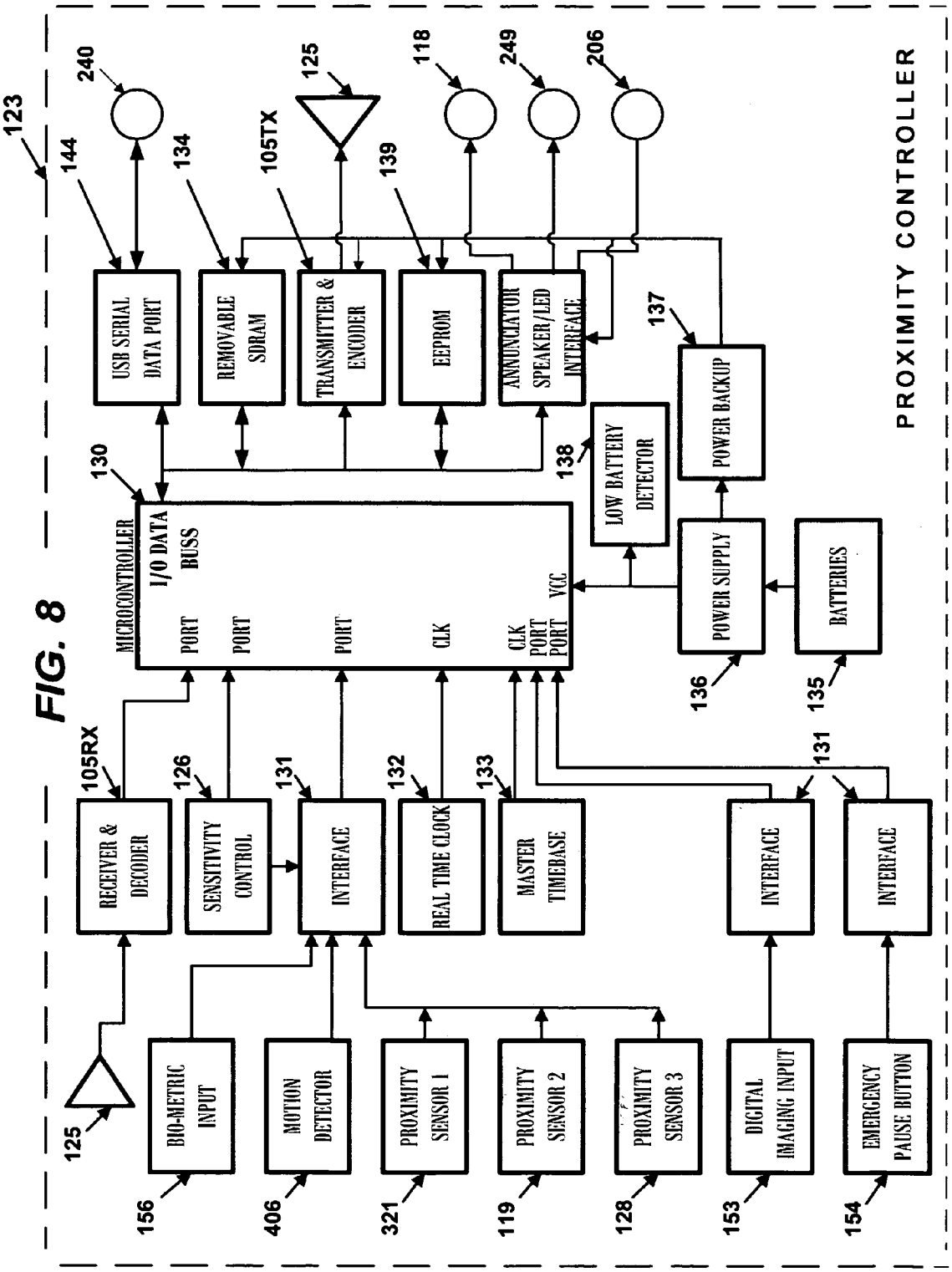
FIG. 8 is a diagrammatic illustration of a proximity controller usable with a hygiene monitoring system.

The proximity controller 123 is shown in greater detail in FIG. 8. This device is capable of sending signals to the HCW monitor 213 and reacting to the receipt of signals 239 from the HCW monitor and/or associated sanitizer by transmitting its own signals 333. The proximity controller 123 includes a power supply 136 with associated batteries 135. An operating system is incorporated in a memory 139. Proximity sensors 119, 128 and 321 and the patient care area motion detector 406, as described above, communicate with an interface 131. Such communication can be wireless or with the use of wires. An emergency pause switch, a power backup 137 and a CPU such as a microcontroller 130 are provided. A real time clock 132 is provided for displaying time and noting the time of possible violations. A removable, non-volatile memory 134, such as an SDRAM, is capable of storing violation data, possibly including video observations of hand washing rule violations. Annunciators 118, 206 and 249 similar to those described above allow visual and/or audio messages to be provided. Other elements of the proximity controller are also found in the patient and/or health care worker monitors, and do not require further description. It will be appreciated that some redundancy is built into the elements of the system described herein, which is preferred but is not considered essential.

Figure 9:
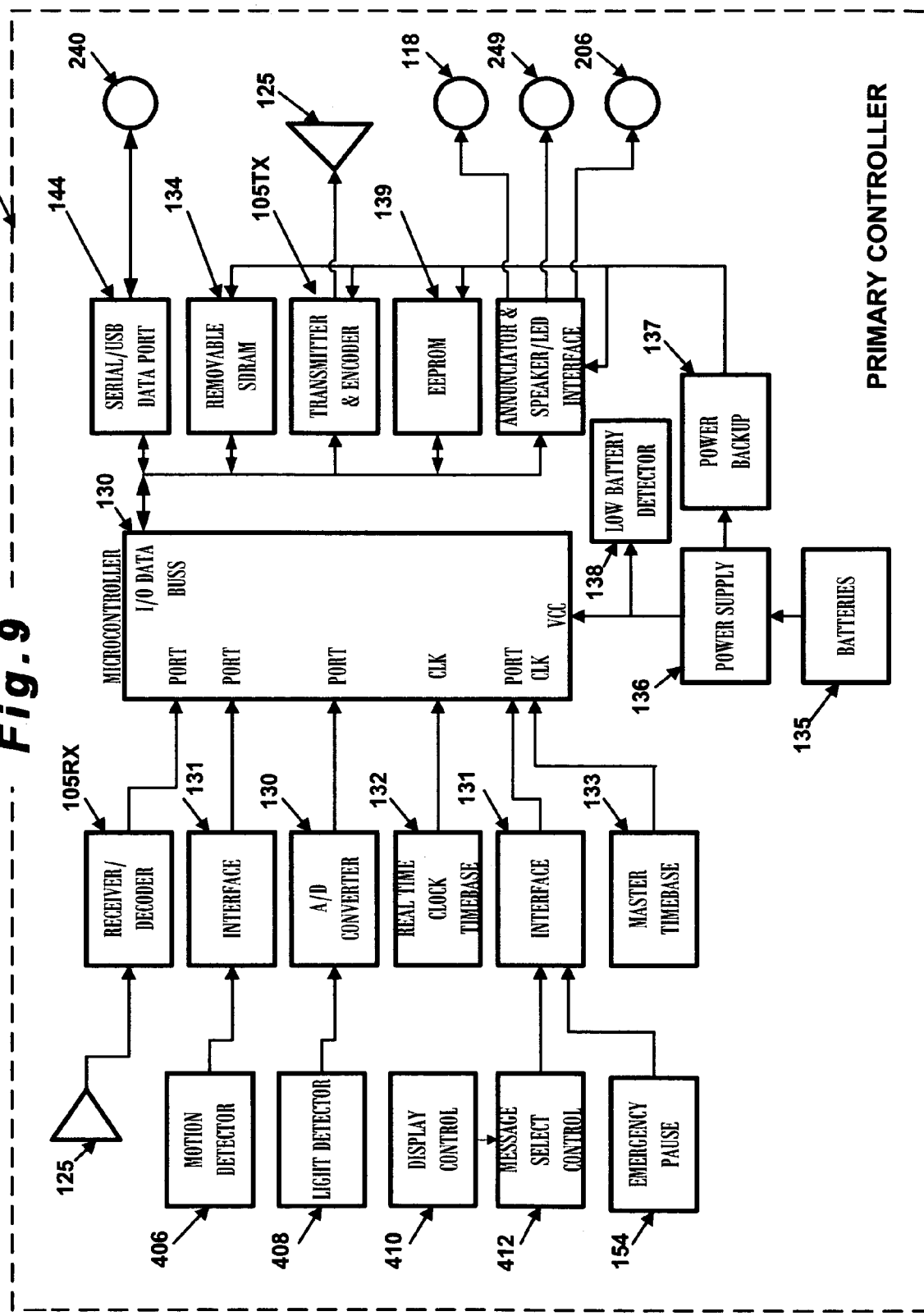
FIG. 9 is a diagrammatic illustration of a primary controller usable with a hygiene monitoring system.

The primary controller 429 is shown in further detail in FIG. 9. It includes a power source such as batteries 135, a power supply 136, a power backup 137 and a low battery detector 138. Notification of a low battery condition is preferably conveyed by means of an indicator, such as the LCD display 118 that is included with the controller. The primary controller 429 includes a CPU such as a microcontroller 130 configured to receive information or instructions from integrated and remote hardware and to cause the operation of other integral or remote devices. The patient care area motion detector 406 is coupled to the CPU by an interface 131. A first memory 139, such as an EEPROM, and a second, preferably removable memory 134 are operatively associated with the CPU. The removable memory 134 may be used to store pertinent patient data such as the patient's name, drug allergies, special care needs and/or other patient-specific information, any or all of which can be displayed on the graphic display 118. A display control 410 is provided for selecting the order and manner in which messages may be displayed upon activation by the patient care area motion detector 406 or upon receipt of signals from the proximity controller 123. Transmitter encoders 105TX, receiver decoders 105RX and antennas 125 provided in the primary controller 429 and proximity controller 123 provide means for wirelessly transmitting and receiving signals between them. A USB connector 240 and associated USB data port 144 allow the controller to be programmed and information to be downloaded.

Figure 12:
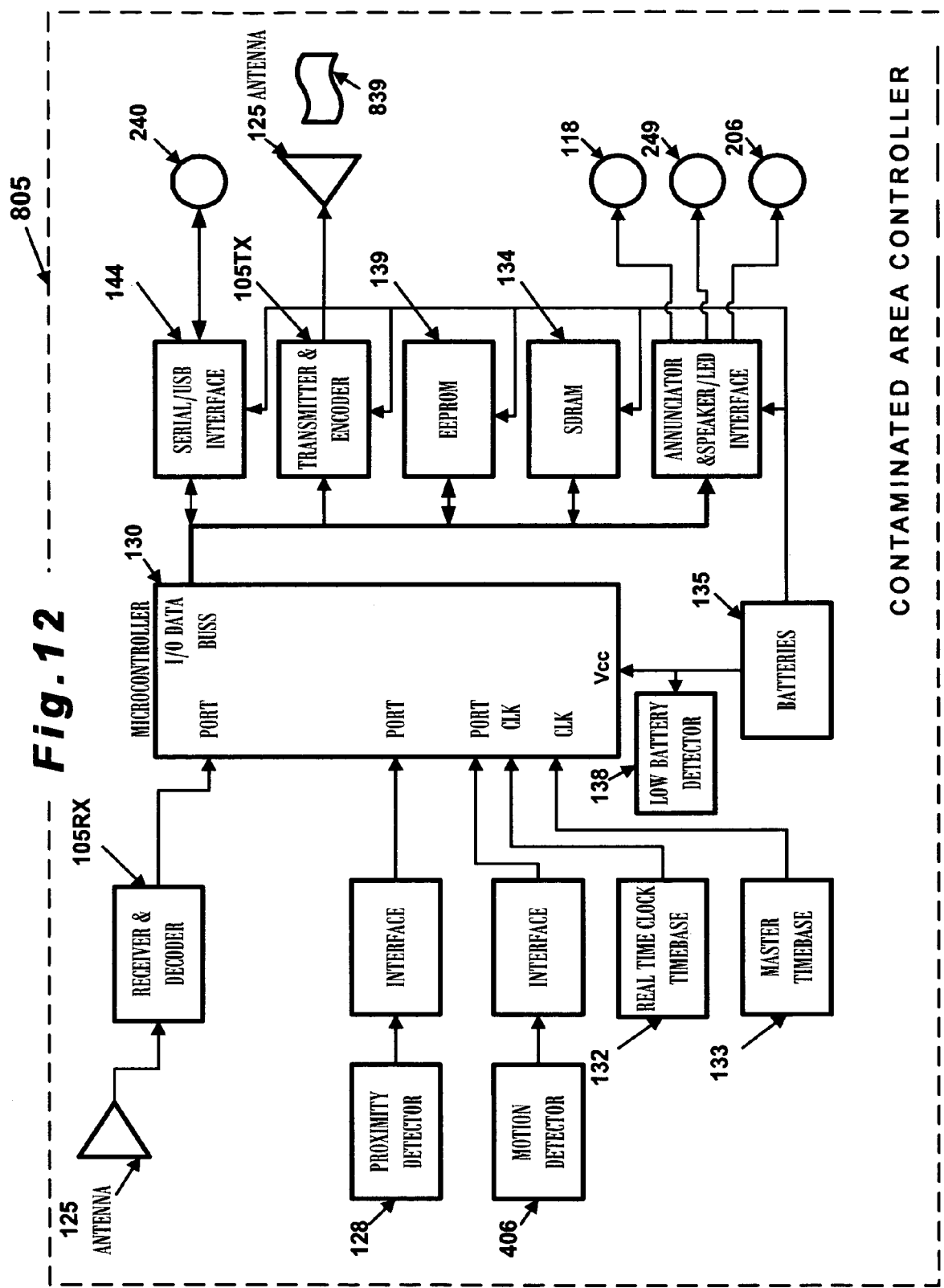
FIG. 12 is a diagrammatic illustration of a contaminated area monitor.

FIG. 12 provides a schematic diagram of the contaminated area monitor 805. This monitor is shown adjoining the entrance to the "contaminated" area 865. The monitor 805 is activated by the motion detector 406 associated therewith or a proximity sensor 128 when a health care worker enters or exits the area 865. The monitor causes a low power signal to be transmitted to the monitor 213, causing the status of the monitor to change to "contaminated", when the worker leaves the contaminated area 865. Actuation of the proximity sensor 128 and motion detector 406 in sequence may be required to cause the low power signal to be generated. Alternatively, such a low power signal may be generated upon actuation of the motion detector 406 alone, which would cause the resetting of the monitor 213 upon a worker entering or leaving the contaminated area 865. The elements comprising the monitor 805 are common to those of other monitors and controllers discussed above, and the same reference numerals are accordingly employed to designate them. It is intended to operate independently of the primary and proximity controllers. While the contaminated area monitor may have displays or the like as shown in FIG. 12, they are not required as the primary purpose of this monitor is to reset the status of the HCW monitor 213.

Figure 13:
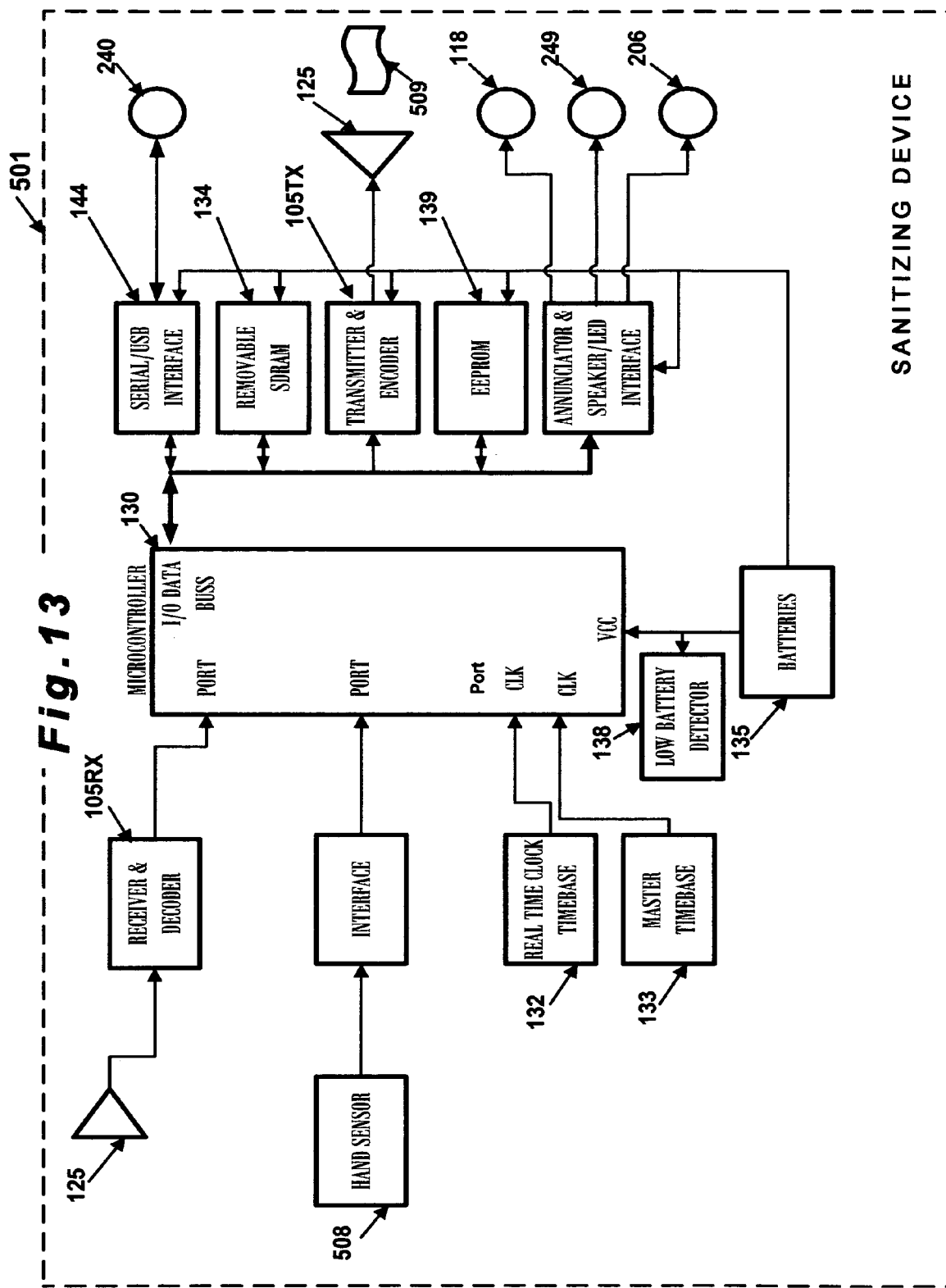
FIG. 13 is a diagrammatic illustration of the sanitizer dispenser shown in FIGS. 7A and 7B.

FIG. 13 includes a schematic diagram of the hand sanitizer 501 employed in the system shown in FIG. 1. As discussed above, it includes a sensor 508 and a dual channel transmitter that, when actuated, will cause the transmission of signals 509, one signal having a relatively short transmission range (e.g. about ten centimeters or less) and another having a longer transmission range (e.g. about fifteen meters or less). The sanitizer is preferably programmed with a discrete code associated with a particular patient, a patient care area 965, or a patient's room or support apparatus. The antenna 125 associated with the transmitter and encoder accordingly transmits an encoded short-range compliance signal 509 that is received by the worker's monitor 213. As discussed hereafter, the worker must preferably use a hand sanitizer associated with the patient or area in order to avoid a warning signal when contacting the patient. The sensor 508 may be an infrared or proximity sensor that, in addition to causing the generation of the signal 509, also causes soap or other sanitizing material to be dispensed. It can alternatively be associated with a mechanical lever (not shown) that causes the compression of the soap-containing bag. The sanitizer 501 further includes a receiver and decoder 105RX with an associated antenna 125. This enables the sanitizer to receive encoded signals from a monitor 213 that will cause the display 118 on the sanitizer to acknowledge receipt of the transmission and the identity of the health care worker. The proximity controller may 123 may additionally or alternatively receive the long range signal 509 from the sanitizer 501. In this manner, the proximity controller may integrate the information regarding the activity of each sensor 508 and the hand washing activity of the health care worker. Appropriate messages may then be displayed on selected annunciators 118 and LED status displays 206. The system accordingly tracks whether persons wash their hands using particular, patient-associated sanitizers and updates compliancy information stored by the monitor 213. As discussed hereafter, a signal from the contaminated area controller 805 causes the monitor 213 to enter a "contaminated" status and display this status until it receives the signal 509 from the sanitizer 501 associated with the patient or room.

Figure 14:
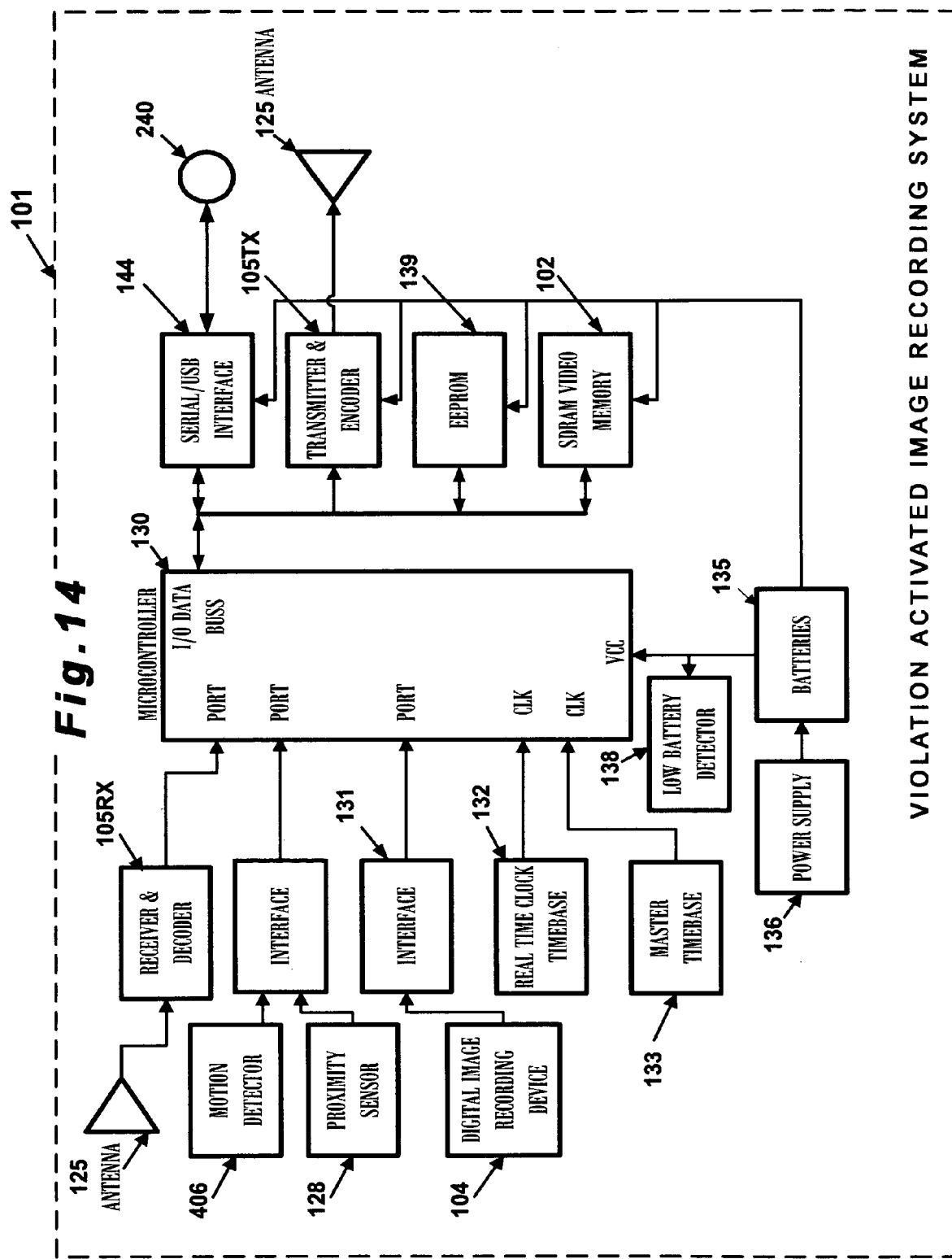
FIG. 14 is a diagrammatic illustration of a video camera usable with the hygiene monitoring system shown in FIG. 1.

FIG. 14 schematically illustrates a motion activated video recording system 101 for recording possible violations of hygienic protocol and/or monitoring a patient for security or other purposes. The system includes a digital image recording device 104 such as a digital camera. It is activated by the proximity controller 123 if it determines that a violation of hygienic protocol has occurred. As discussed below, the recording system can also be activated upon placing the system 100 in a standby mode. Recorded images may be transmitted wirelessly and/or stored in a static random access memory 102. Upon actuation of the system, either a single image may be taken or a series of images may be taken over a selected period of time.

Figure 15:
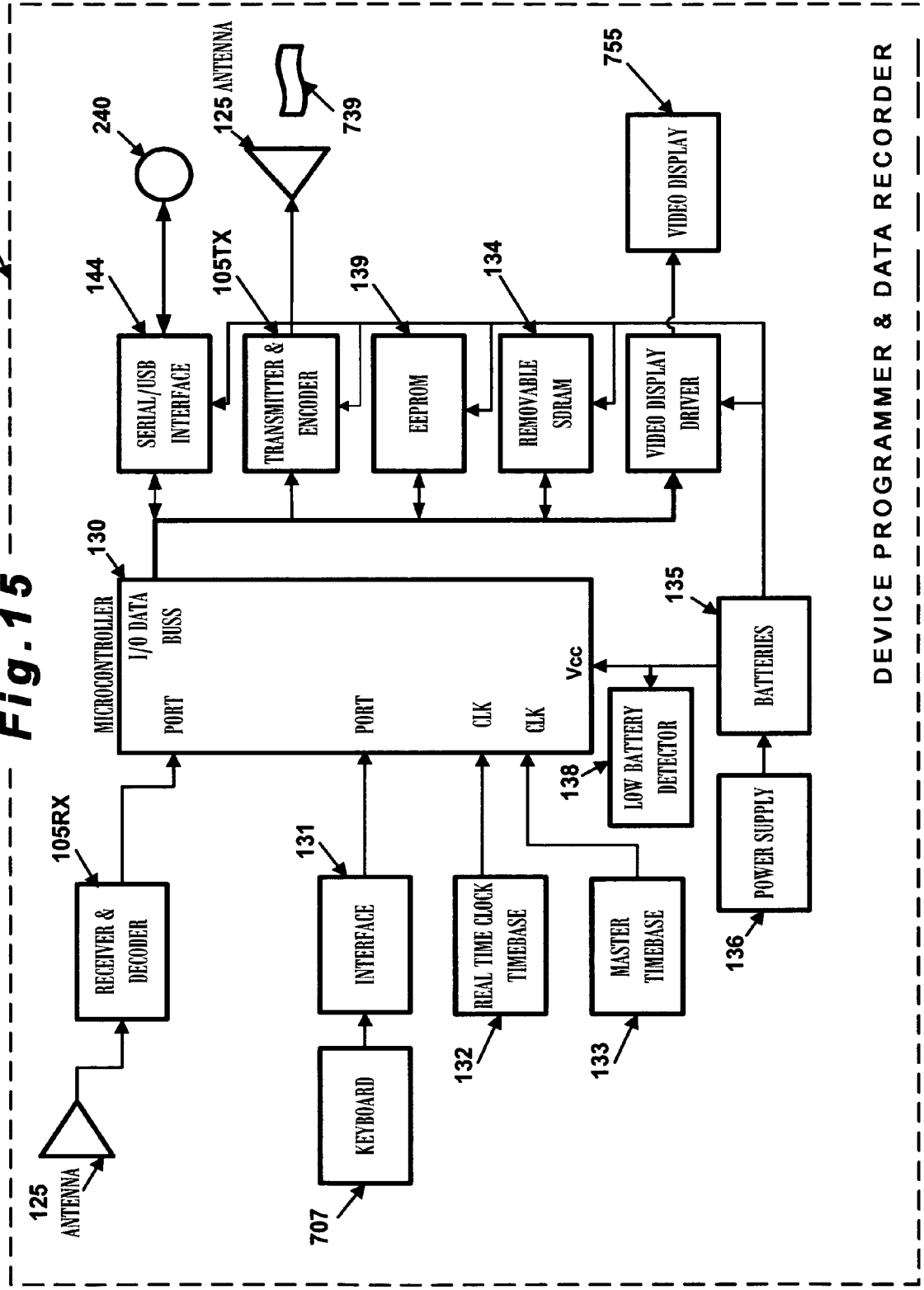
FIG. 15 is a diagrammatic illustration of a data programmer and recorder usable with a hygiene monitoring system.

A data programmer and recorder 701, as schematically illustrated in FIG. 15, is provided for programming the HCW monitor 213 and patient monitor 313 as well as for receiving data from these monitors. The patient monitor 313 may be pre-programmed with information such as the patient's name and pertinent medical data. Programming and retrieving data from and to the patient monitor 313 and the removable memories 134 associated with the proximity controller 123 and primary controller 429 may be accomplished via a USB serial data port 144 and associated connector 240. The data programmer and recorder 701 includes a keyboard 707, a CPU (microcontroller 130), an operating system (EEPROM 139), a video display 755 and a transmitter 105TX capable of communicating a discrete identifier code and data related to a patient such as the patient's name and special care instructions for that patient. The HCW monitor 213 can be programmed with data as well, including the identity of the health care worker who will be wearing the monitor. Similarly, data relating to the patient may be recorded on a memory card (removable SDRAM 134) and subsequently inserted into the proximity controller 123. Alternatively, patient data may be directly loaded into a data card while in place in the proximity controller 123 via wired or wireless means. Communications between the patient monitor 313 or the HCW monitor 213 and data programmer and recorder 701 may be accomplished by hardwire via the USB port and/or wirelessly via the transmitter 105TX and receiver 105RX and associated antennas 125. If wireless transmission is chosen, the monitors are placed on or near the data programmer and recorder 701. The data remains in residence as non-volatile memory within the monitors until a special code is transmitted by the data programmer and recorder 701. Once data is retrieved by the data programmer and recorder, the collective data from a plurality of monitors may be transferred to a removable data storage card or transferred directly to a central processing unit.

When a new patient is placed in a bed in the patient control area 965, a patient monitor is reprogrammed using the data programmer and recorder 701 prior to being affixed to the patient. The proximity controller 123 would receive a communication from the patient monitor 313, allowing it to determine that the code for the patient monitor has changed and that a new patient is present.

The firmware incorporated by the data programmer and recorder 701, when executed by the CPU logic, generally causes the associated memory 134 to record data from the HCW monitor 213, the patient monitor 313, visitor monitor 620 (FIG. 18), proximity controller 123 and video images of violations relating to the collective compliance of persons with a hygiene policy such as institutional hand washing rules. More specifically, the CPU logic is operable to generate a data file ultimately resulting in the generation of a compliance report based on the processing of the inputted data.

Figure 17:
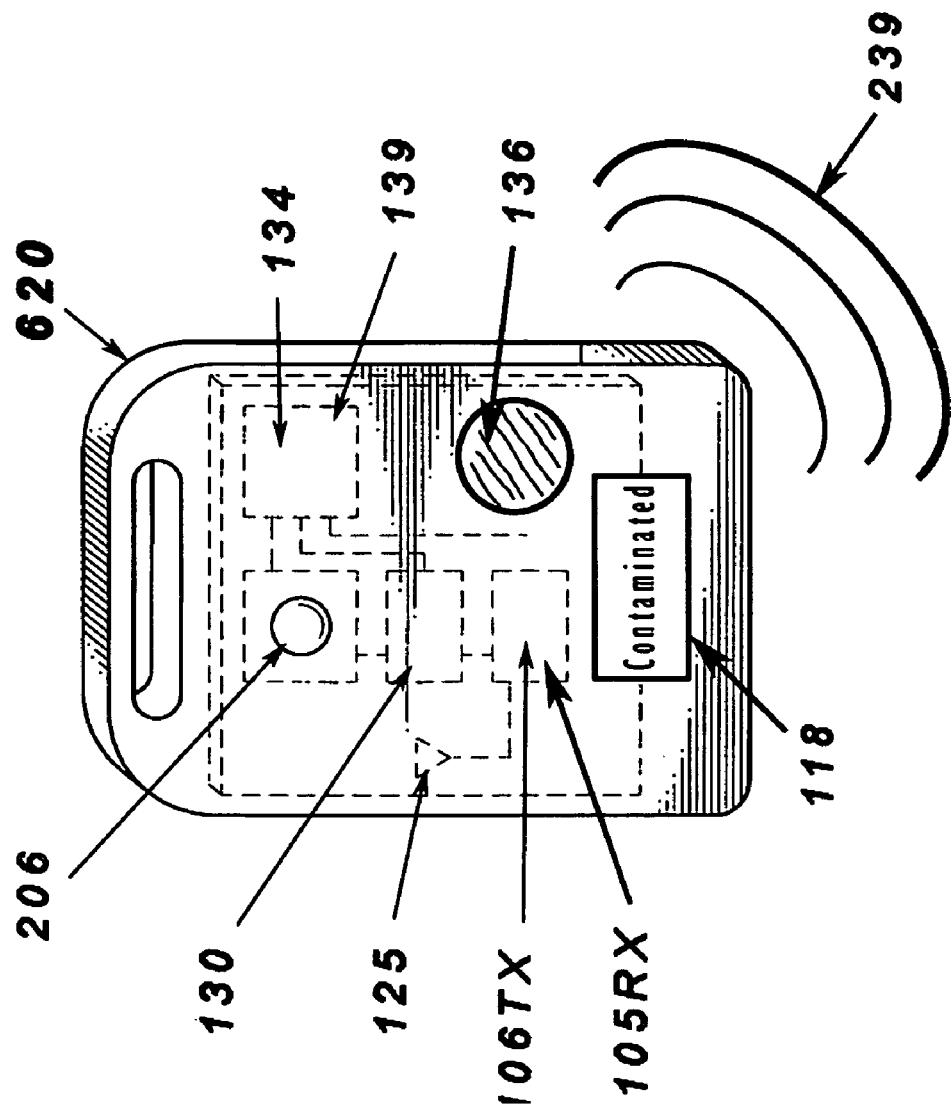
FIG. 17 is a top perspective view of a visitor monitor usable within a hygiene monitoring system.

FIG. 17 shows the visitor monitor 620. This monitor can be affixed to a chain or cord (not shown) and worn around the neck and/or include a clip (not shown) for fastening it to the visitor's clothing. The visitor monitor includes a number of elements common to the patient and HCW monitors, including a central processing unit 130, a memory 139 including an operating system, a removable memory 134, an LCD display 118, an LED display 206, a transmitter 105TX for transmitting a signal 239 to the proximity controller 123, and a receiver 105RX for receiving a signal 333 from the proximity controller 123. The visitor monitor could have the same capabilities as the HCW monitor and be programmable in the same manner, but would not necessarily include specific identification information relating to the visitor.

Figure 6:
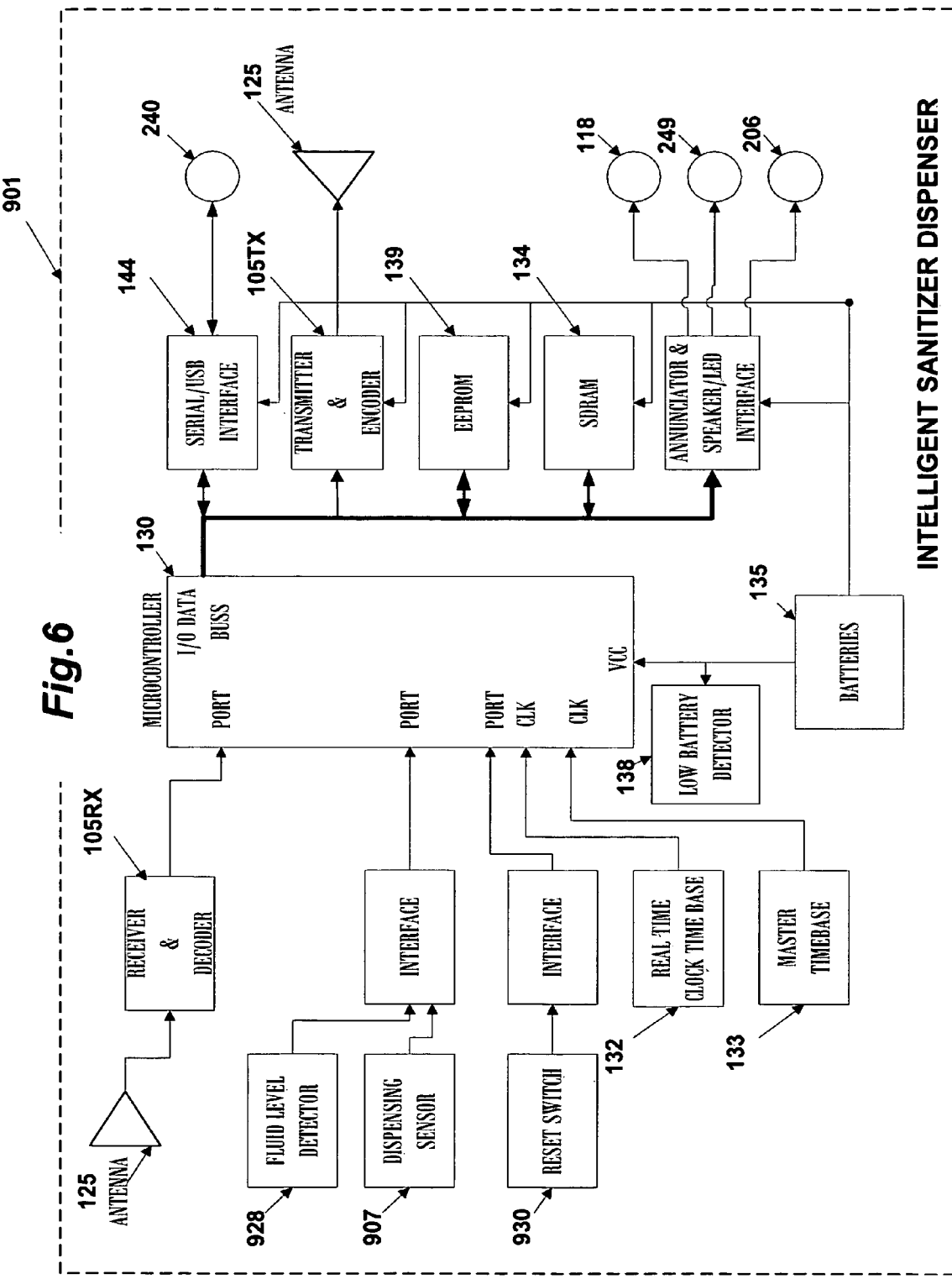
FIG. 6 is a diagrammatic illustration of a sanitizer dispenser usable with a hygiene monitoring system.

An alternative embodiment of the hand sanitizer is shown in FIGS. 6, 7A and 7B. This hand sanitizer 901 may be used in place of or in addition to the hand sanitizer 501 described above. The sanitizer 901 is designed for portability, and could perform the functions of the HCW monitor 213 and the wall-mounted sanitizer 501, thereby obviating the need for both. It could be designed to fit in a pocket or affixed to a belt or other article of clothing. Unlike the sanitizer 501 described above, the portable sanitizer 901 would not be associated with a particular room or patient. A pump-type dispenser is shown in the drawings, though other mechanisms for dispensing sanitizing material can alternatively be employed. The sanitizer includes a sensor 907 to detect when sanitizing material has been dispensed. This sensor could, for example, detect a change in pressure in the container portion of the sanitizer when the pump is actuated. Upon activation of a proximity sensor 128 by a health care worker, the proximity controller 123 sends a signal 133 to the receiver 105RX in the sanitizer 901, causing a message to be generated on the LCD display 118 on the sanitizer 901. A warning or other alert could be similarly displayed on the display 118 associated with the primary controller 429 if the system includes such a controller. Logic in the CPU 130 and memory 139 of the sanitizer 901 may be provided to preclude the generation of a compliance signal by the sanitizer back to the proximity controller prior to activation by the signal 133 from the proximity controller 123. The sanitizer preferably must be employed immediately following activation of the proximity sensor 128 such that its operation is in close proximity to the patient. (In contrast, the wall-mounted sanitizer 501 as discussed above is activated prior to the health care worker's detection by one of the proximity sensors 128.

As shown in FIG. 6, the sanitizer 901 may include other means of communicating warnings, such as an LED display 206, a speaker 249 and/or a vibration mechanism (not shown). The warning mechanisms are preferably designed to avoid disturbing a sleeping or resting patient while providing adequate prompting to the health care worker to wash his hands. Other features of the portable sanitizer disclosed herein include a fluid level detector 928 and a reset switch 930. The reset switch 930 can be used to override violation warnings and/or messages, but such activation is preferably noted as a violation of hand washing rules and results in the recording of such action in the memory 134 and/or by the digital imaging system 101.

The system including the portable sanitizer 901 and multiple proximity sensors ensures that the health care worker will be in a patient care area 965 in close proximity to the patient when requested to sanitize his/her hands. The system may further provide the health care worker with the option of not using the sanitizer 901 while still remaining within the hand washing rules if the immediate actions that are to be taken by the health care worker do not involve patient contact. For example, if the health care worker is simply viewing a medical apparatus associated with the patient and does not cause the activation of the proximity sensor 119 on the rail and/or the contact sensor 321, no warning is generated and a violation of the rules would not be recorded. If contact with the patient is made and sanitizing material has been dispensed within a predefined period subsequent to receipt of the signal 333 from the proximity controller 123, a signal 239 will be transmitted from the sanitizer 901 to the proximity controller. This will preclude any action on the part of the proximity controller that would cause the indication or recordation of a violation regardless of subsequent activation of additional proximity sensors. If, however, the health care worker has not so actuated the sanitizer 901 within the required time or distance from the patient, as noted by the absence of a generated signal 239, the proximity controller 123 will cause a record of a violation to be made and generate a warning signal upon receipt of signals from proximity sensors 119 and/or 321. It may also cause a warning signal to be generated or displayed on the sanitizer 901. While the preferred system requires hand sanitation within a predetermined time as well as within a predetermined area, it can be configured to operate without a time requirement so long as the sanitizer 901 is actuated within the patient care area 965 before the health care worker comes into close proximity or contact with the patient.

As mentioned above, the portable sanitizer 901 may instead be programmed to perform the functions of the HCW monitor 213. It could be responsive to signals 839 from the contaminated area controller 805 that would cause it to display a contaminated status. If the portable sanitizer is actuated following the worker being detected by one of the proximity sensors 128, the status is changed to uncontaminated and an appropriate signal is sent to the proximity controller 123. If the worker has not washed his hands, the status will remain "contaminated" and a violation will be noted if he is detected by one of the closer proximity sensors 119 and/or 321.

While the use of proximity sensors 128 is preferred in all embodiments of the invention, the proximity controller may be activated by other means that determine the location of the sanitizer 901 and/or monitor 213 and their associated health care worker. Such means may include multi-node radio location systems such as ZigBee (not shown), Bluetooth, Wi-Fi, or GPS (not shown). The system 100 preferably allows for simultaneous monitoring of multiple contiguous areas. Proximity sensors 128 may surround a patient's bed and define one patient care area 965 from other patient care areas that may be within a room. The proximity sensors 128 may include sensor plates configured as floor tiles, hidden wires, visible electrically conductive tape that surrounds the bed 924, or other suitable sensors. In a typical hospital situation where more than one bed is located in a room, conventional motion detectors or RF triangulation may not provide the geometry and resolution to differentiate one patient area from another. Proximity sensors are accordingly preferred for this purpose. The system 100 employs a combination of motion detectors and proximity sensors to determine the proximity of a health care worker or other person to a patient in multiple increments of increasing or decreasing proximity. The sequence of activation of the aforementioned detectors and sensors allows the CPU logic of the proximity controller 123 to ascertain the direction of movement of a health care worker and respond with the appropriate actions. The configuration of proximity sensors facilitates determining hand washing rule compliance such that audible and/or visual responses related to the specific distance and direction of travel of the health care worker to and/or from the patient can be made.

The manner in which the elements described above relate to each other is generally shown in FIG. 2. Two types of sanitizers 501, 901 are shown in the figure. While both stationary and portable sanitizers can be incorporated within the system 100, only one type is necessary. If two types are used, they should be programmed so that they function in a complementary manner with the monitors and proximity controller.

Figure 3:
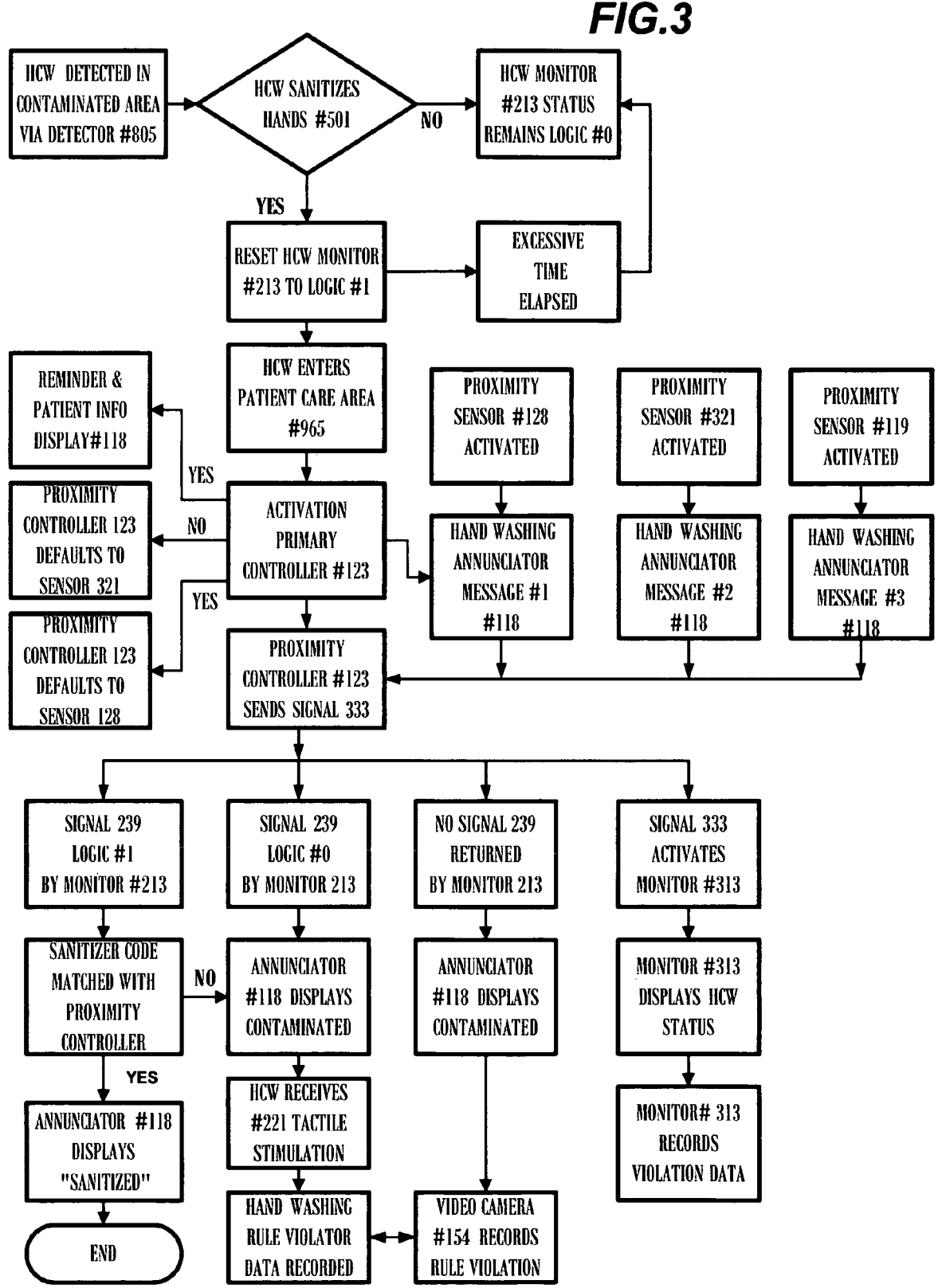
FIG. 3 is a flow diagram showing the operation of a hygiene monitoring system.

Referring to FIG. 3, a flow chart illustrating the operation of the system 100 is shown. As discussed above, the elements of the system are designed to determine whether hand washing protocols have been followed, and to cause selected signals to be generated and certain information recorded depending on whether a health care worker or other person has been compliant. Various situations may occur, which will cause the system to react in different ways.

Example 1

In a first situation, a health care worker wearing a monitor 213 enters a room and is detected by the motion sensor 406 associated with the controller 805. In this example, the room is considered a contaminated area 865. The worker will be considered "contaminated" when he enters (or leaves) the contaminated area and the controller 805 accordingly generates a low power signal to the monitor 213 (or sanitizer 901 if a portable sanitizer is used instead of a monitor 213). This signal causes the monitor to set to Logic #0. (It will be appreciated that the monitor will be already have been set to Logic #0 if the worker has previously been detected in any contaminated area without washing his hands or if too much time has elapsed since the previous hand washing.) The worker may proceed to perform duties within the room that are not in close proximity to the patient without receiving a warning or causing a violation to be noted though he has not washed his hands. Even if detected by the motion detector 406 associated with the proximity controller 123, the preferred system further requires detection of the worker by one of the proximity sensors in order to cause the generation of warning signals and/or cause the recording of a violation. Detection of the worker by the patient care motion detector 406 will cause a hand washing reminder or other message to be displayed on or broadcast by the primary controller 429, but no warning signals are generated or violations recorded upon such detection.

Example 2

In a second situation, a health care worker enters a patient's room and then uses the hand sanitizer 501 in accordance with required hygienic protocol. The sanitizer generates a signal 509 that causes the worker's monitor to reset to Logic #1 from Logic #0 and the monitor display 118 to show a message indicating hand washing compliance. The health care worker then proceeds to the patient care area 965, first being detected by the patient care area motion detector 406 associated with the proximity controller 123 and then by one or more of the proximity sensors 128, 119, 321. The monitor 213 is queried by the proximity controller 123, which generates a signal 133 upon sequential actuation of the motion detector 406 and one of the proximity sensors. An encoded signal 239 indicating compliance with hand washing protocol is returned by the monitor 213. The display 118 associated with the proximity controller 123 is caused to generate a message such as "Sanitized." Activation of the proximity sensors may also cause other information to be displayed by the proximity controller display and/or patient monitor 313 such as the patient's name, drug allergies or special care requirements. This type of information can be displayed without such activation if desired, or through the use of other worker or patient-operated controls (not shown).

Example 3

In a third situation, a health care worker enters a patient care area 965 and a hand washing reminder message is displayed by the primary controller following detection by the patient care area motion detector 406. The worker, in this case, has washed his hands using the sanitizer 501 associated with the patient and/or room, but has allowed too much time to elapse since such washing. The display 206 on the monitor 213 is accordingly caused to illuminate or flash to signify that excessive time has elapsed, and the monitor status changes from Logic #1 to Logic #0. The worker then proceeds to near proximity of the patient, i.e. within arms length of the patient or bed, and is detected by one of the proximity sensors 128. This causes the proximity controller 123 to transmit an encoded signal 133 requesting a response signal from the monitor 213. The monitor 213 then transmits an encoded signal reflecting the Logic #0 status of the monitor. Upon receipt of this signal by the proximity controller 123, a caution message is displayed on one or more of the annunciators 118, 206 associated with the proximity controller. Subsequent activation of one of the proximity sensors 119 and/or 321 causes the proximity controller 123 to display a warning message on its LCD display 118. If the health care worker does not vacate the patient care area 965 within a certain period of time, an audible alarm will be generated by the speaker 249 associated with the proximity controller. An appropriate message may also be displayed on the monitor 213 and/or tactile stimulation by the vibrating mechanism 248 or electro-stimulator 221 contained in the monitor 213. Violation information, including time, patient identification and worker identification will be recorded in the memory 134 of the monitor 213 and/or the proximity controller 123.

Example 4

A fourth possible situation involves a patient development that requires immediate attention. A health care worker enters the patient care area 965, is detected by the patient care area motion detector 406 associated with the proximity controller 123, and receives a cautionary or reminder message on the display 118 of the primary controller 429 and/or the proximity controller 123. The worker has not washed his hands, and his monitor 213 is set to Logic #0 in the manner described above. He then comes in close proximity to or contact with the patient, as detected by a proximity detector 128, 119 and/or 321. The proximity controller 123, having queried the HCW monitor, receives a signal from the monitor 213 signifying the worker has not complied with hand washing rules. It then causes warnings to be displayed on its own display 118 and/or the displays provided on the worker and patient monitors 213, 313. In order to allow the worker to proceed without distraction, the system 100 may be placed in a standby mode by activating the pause switch 154 located on the primary controller 429 or proximity controller 123 or the standby switch 247 on the worker's monitor 213. This action causes a resetting of the system 100 to a standby status as well as causing the primary controller and/or proximity controller to replace their warning messages with messages declaring that an emergency is in progress. No further warnings, alarms, or other messages will be caused to be displayed on the monitors 213, 313 or other components of the system until it is reset to the normal operating mode. The actions in the patient care area 965 subsequent to placing the system in a standby mode may be recorded by the video recording system 101, preferably automatically. The placing of the system in standby mode can also be recorded elsewhere in the system, such as in the memory of the proximity controller and/or the worker monitor 213.

Example 5

A fifth situation may occur should the health care worker need to stay in the patient care area 965 for an extended period of time. There are circumstances that may require repetitive contact with a patient that would involve multiple activations of the patient proximity sensors 128, 119 and/or 321 while the health care worker does not exit the patient care area 965 and/or enter a new contaminated area within an extended period of time. In order to avoid repetitive triggering of the proximity controller 123 and primary controller 429, causing corresponding warning signals to be generated, the health care worker may elect to employ the standby switch 247 on his monitor 213 to continue working after the preset time has run out since the previous use of the patient-associated sanitizer 501. The monitor will be reset to Logic #3 when the standby switch 247 is employed to prevent subsequent activation of the proximity controller as the proximity sensors detect the worker. Resetting the system 100 to its normal operational mode may be accomplished by the worker departing the area monitored by the motion detector 406 associated with the proximity controller 123, by a signal from the data recorder 701, by pushing the pause switch 154 on the proximity controller or by resetting the health care worker monitor 213.

Example 6

In a sixth situation, a person who is not wearing a monitor 213 enters the patient care area 965 where he is detected by the patient care area motion detector 406. The primary controller display 118 is caused to generate a preselected message such as a hand washing reminder. The person proceeds to the patient where he is detected by a proximity sensor 128. The proximity controller 123, having received input signals from both the patient area motion detector and then a proximity sensor within a predetermined period of time, transmits a signal 133 requesting a response from a monitor 213 (Logic #1) to confirm compliance with hand washing protocol. Upon receiving no such signal whether the person has used the sanitizer 501 or not, a warning signal is generated by one or more of the annunciators in the system 100. If the person does not leave the patient care area 965 monitored by the proximity sensors 128 within a certain time or causes the triggering of one of the closer proximity sensors 119 or 321, a more compelling warning can be generated by the system and the nursing station can be alerted. If, as in this example, the absence of a monitor is considered a violation of protocol, the event and its time are recorded by the patient monitor 313 and/or the proximity controller 123. The video recording system 101 may also be activated, causing the video camera 104 to record the violation and store the recorded data in the memory 134 of the proximity controller 123. The person's exit from the area monitored by the proximity sensors 128 and/or the patient care area motion detector 406 allows the system 100 to return to its normal operating mode, and video recording will discontinue immediately or a short time thereafter.

Example 7

In a seventh situation, a visitor enters the patient care area 965 while wearing a visitor monitor 620 as shown in FIG. 17. The visitor is detected by the patient care area motion detector 406, causing the primary controller 429 to display a message reminding the visitor to wash his hands. The visitor then employs the sanitizer 501, causing the display 206 on the monitor 620 to provide a compliance indication. The visitor, having complied with the required hand washing protocol, proceeds to within arms length of the patient and is detected by a proximity sensor 128. The proximity controller 123, having received input signals from both the motion detector 406 and proximity sensor 128 within a predetermined period of time, sends a signal 133 that is received by the monitor 620, which transmits a signal 239 back to the proximity controller. Receipt of the signal 239 causes a message to be generated by the LCD display 118 on the proximity controller 123. The message can thank the visitor for washing his hands, remind the visitor to keep the visit short, and/or provide other information such as patient visiting hours. Subsequent activation of the other proximity sensors 119, 321 can cause the generation of further messages on the visitor monitor and/or the proximity controller 123 such as a reminder to wash his hands again upon departure.

The system 100 can operate without a primary controller 429 as it is somewhat redundant to the proximity controller 123. The primary controller, if employed, can operate independently from the proximity controller or be linked thereto by wired or wireless connection. It can be combined with the sanitizer 501. In order to avoid disturbing a sleeping patient, the primary and proximity controllers can be programmed so that they do not cause the patient to be disturbed when a health care worker enters the patient care area. For example, the illumination of displays can be reduced during nighttime hours and audible signals eliminated during such time. The displays can be located in parts of a room where a resting patient will not be disturbed by them or where they are positioned or shielded from a patient's view.

Continuous monitoring of the patient is provided by the system 100 irrespective of whether the persons who may come into contact with the patient are wearing monitors or not. Such monitoring is accomplished with minimal power requirements and extended battery life as the entire system is effectively in a "sleep mode" until a specific action is taken that causes detection by a motion detector or a proximity sensor.

As discussed above, hand sanitizing is accomplished through the use of either stationary or portable sanitizers. The sanitizer 501 as described above transmits a signal 509 to the monitor 213 upon actuation of the sensor 508, causing an indicator 206 on the monitor 213 to change appearance as well as the display 118 on the sanitizer to indicate compliance with the institution's hand washing protocol. Patient hand washing can be encouraged in a similar manner by interactions between the sanitizer 501 and patient monitor 313. The sanitizer 501 is also capable of receiving a signal from a monitor 213,313 that is generated in response to the signal 509. The monitor signal includes identification information that allows the identification of the person using the sanitizer to be recorded. Since the compliance signal 509 has a short transmission range, preferably ten centimeters or less, it is unlikely to trigger a response from any monitor other than that worn by the person using the sanitizer 501. The longer range signal 509 from the sanitizer is processed by the proximity controller 123 as opposed to a monitor 213. When queried by the proximity controller 123, the signal transmitted by the monitor may include user identification information as well as compliance information relating to use of the sanitizer 501. Since the proximity controller 123 may receive the signal 509 directly from the sanitizer 501 in the preferred embodiment, the proximity controller may integrate the information regarding the activity of each sanitizer and the hand washing activity of the health care worker. The monitor 213 would then only need to transmit identification information to the proximity controller when queried, and the proximity controller would determine whether the person wearing the monitor washed his hands within a preset period of time.

The monitoring of hand washing compliance may be accomplished through means other than the sanitizing devices as disclosed. For example, a sensor may be incorporated as part of a sink and faucet assembly for determining whether a person has washed his hands. A successful hand washing may occur when the person has stood before a sink for a selected period of time, dispensed soap, and/or used a drying unit. Hand washing sensors and associated transmitters of compliance signals may also be included in devices such as automated alcohol or alcohol towelette dispensers, antiseptic dispensers, UV lights, glove dispensers or other monitored devices that may be used to sanitize hands.

In the preferred embodiment, the HCW monitor 213 is associated with a particular worker and the sanitizer 501 is associated with a particular patient, room or patient care area. When the health care worker enters the room, his monitor, if not in Logic #0, is set to Logic #0 by the contaminated area monitor 805 upon detection of the worker by the contaminated area motion detector 406. When the worker approaches a patient, thereby first triggering the patient care area motion detector 406 and then a proximity sensor 128, the proximity controller 123 generates an encoded handshake signal 133. Assuming the worker is wearing a monitor 213 or portable sanitizer 901, a response signal 239 is transmitted to the proximity controller 123 that includes the worker's identity and the identity code of the sanitizer 501 or 901 associated with his most recent hand washing event. Upon receipt of the signal 239, the proximity controller 123 will compare the sanitizer identity code with pre-programmed acceptable codes associated with the patient. If the code is acceptable, the display 118 on the proximity controller can signify compliance with the institution's hand washing protocol. As discussed above, the system may be configured such that the sanitizer 501 communicates directly with the proximity controller 123, providing sanitizer identification information thereto as well as the identification of the user of the sanitizer. The monitor signal may then include only an identification code for the worker, and the proximity controller will determine whether that worker has used a particular sanitizer within a selected period of time. A record can be made of the worker's proper use of the sanitizer and stored in the proximity controller memory 134. Similarly, when the proximity controller is caused to generate a signal 133 and it either fails to receive a response or receives a response indicating non-compliance (Logic #0), such action will cause the generation of contamination warnings and record the time of the violation, the identity of the violator if he is wearing a monitor, and the identification of the patient. It may also cause the actuation of the video camera 104, thereby identifying any violator who may not be wearing a monitor.

In lieu of using a monitor 213 or similar device to transmit worker identification information to the sanitizer, the identity of the health care worker may instead be provided to the sanitizer 501 by RFID, biometric means (not shown) such as fingerprint recognition, an identity card with a magnetic strip or bar coding, or keypad input. The health care worker identity and the specifics of the hand washing event are then recorded by the sanitizer and transmitted to the proximity controller 123 for subsequent comparison to an identity input by the worker upon reaching the patient care area 965 or entering the area monitored by the proximity sensors 128. This action can be accomplished following prompting from the display 118 of the primary controller 429 or upon activation of a proximity sensor 128. The matching of the worker identity and preferred sanitizer identity by the proximity controller upon the timely re-entry of the worker identity into the proximity controller 123 will confirm compliance with the required hand washing protocol.

The patient area motion detector 406 and the proximity sensors 128, 119 and 321 may be employed for causing the proximity controller 123 and/or the primary controller 429 to generate different messages as described above. Sequential activation of the motion detector 406 and then, shortly thereafter, one of the sensors 128, 119 and/or 321 will cause the proximity controller 123 to determine that a person is approaching a patient and attempt to determine whether that person has complied with required hand washing procedures. Activation of solely the patient care area motion detector only causes the primary controller 429 to generate a message advising the worker that the area is monitored and/or reminding the worker to wash his hands if he intends to contact the patient. The field of view of the motion detector 406 is configured via a lens or baffles such that it is very unlikely to be activated by the patient while in bed. Activation of sensors 119, 128 or 321 without prior recent activation of the motion detector 406 may be assumed to be caused by the patient, and the proximity controller is programmed to cause no messages or signals to be generated in response thereto. It may be desirable to generate a signal or message if one of the sensors 128 is actuated even without prior recent activation of the motion sensor since it is more unlikely for the patient to activate these sensors than the other two. While the sensors 128 communicate with the proximity controller 123 in the preferred system, they and the motion detector 406 could additionally or alternatively communicate directly with displays capable of providing advisory or warning messages to a person in the patient's room. The use of proximity sensors 128 that detect persons in close proximity to a patient (i.e. within arms length of the patient or the bed) but are not likely to be actuated by the patient while in bed is preferred for successful operation as only a health care worker or visitor will be likely to sequentially activate the motion detector 406 and a sensor 128 within a short period of time. Moreover, such an arrangement helps ensure that warnings will not be generated or violations recorded by anything other than a person who comes in the room to actually treat or contact the patient.

The proximity sensor 321 is operatively associated with the patient, and will accordingly remain with the patient whether he is in bed or elsewhere. It is intended to sense when a person is in near contact with (within about five centimeters or less) or touching a patient or an article worn by, covering or otherwise contacting the patient. One type of sensor that may be employed for such sensing is a charge-transfer (QT) sensor. When a person either touches or comes very close to the sensing electrode(s) of such a sensor, a change in capacitance is sensed. The QT110 sensor produced by Quantum Research Group is one type of proximity sensor that may be incorporated within the patient monitor 313. It also provides digital processing capability for rejecting impulse noise. The housing of the patient monitor 313 and/or the outer surface of the associated strap may include metal portions and function as sensing electrodes. The patient's body may function as the sensing electrode with the contact pins 325 providing an electrical connection between the patient's skin and the sensor 321. The proximity sensor 321 may be located outside the monitor 313 and its associated sensing electrode(s) may be affixed to the patient's clothing or elsewhere on an article contacting the patient. The sensor 321 is preferably worn by the patient and therefore usable wherever a patient may be located within the institution. While preferably employed in combination with the motion detector 406 and/or other proximity sensors to avoid false alarms, it can be used without such other detectors if located and designed such that the patient is unlikely to cause its triggering himself.

In addition to promoting hygienic compliance, the system 100 may be employed for restricting access to a monitored area to a selected group of personnel. The system provides the means for detection of all persons entering such an area irrespective of whether they are wearing monitoring devices or not. A restricted access area may be a designated patient area 965 in which a highly contagious patient is located or a neonate ward. Proximity sensors 128 such as those described above surround the monitored area, and may or may not be visible. The restricted area can be rectangular, but does not necessarily have to be in any particular geometric form. A motion detector 406 is preferably employed to provide additional logic, as described above. A digital recording system 101 records violations as determined by a proximity controller 123. The motion detector 406 will initially recognize the presence of a health care worker or any other person within a general predefined area to the exclusion of the patient or neonate due to its physical location and/or the use of a shield 155. This may cause the primary controller 429 to display a message conveying the fact that the area is monitored. Once a proximity sensor 128 detects the presence of a person by a disturbance of its field of sensitivity, the proximity controller 123 will transmit a signal 133 and subsequently search for a responding monitor 213. Upon receiving a signal 239 from such a monitor 213 that has been pre-encoded to permit access to the restricted area, a message indicating access compliance will be displayed by the proximity controller and/or the primary controller. If a properly encoded signal 239 is not received by the proximity controller 123, a warning can be displayed indicating that an unauthorized entrance has been made. The digital image recording device 104 can also be actuated to record the activity of the violator on the memory 134 of the proximity controller 123 or elsewhere. Additional proximity sensors may be employed to further define the restricted area and to possibly cause the generation of additional warnings or alarms.

All monitors, sensors, sanitizers and other elements of the system 100 are preferably designed for easy cleaning or disinfecting. Bactericidal materials may be incorporated into the monitors or portions thereof to help ensure patient and worker safety.

What is claimed is:

1. A method for promoting hygienic practices comprising:
   providing a monitor capable of transmitting information;
   detecting a person in close proximity to or in contact with a patient regardless of whether the person possesses the monitor;
   determining through operation of a processing assembly whether the person possesses the monitor and has actuated a sanitizing device; and
   generating a caution or warning signal unless the person in close proximity to or in contact with the patient possesses the monitor and has actuated the sanitizing device.

2. A method as described in claim 1 further including the steps of first detecting the person within a selected non-proximate distance of the patient in a room occupied by the patient regardless of whether the person possesses the monitor and then second detecting the person in close proximity to or in contact with the patient, and generating the caution or warning signal if the person is sequentially detected during said first detecting and second detecting steps unless the person possesses the monitor and has actuated the sanitizing device.

3. A method as described in claim 2 further including the step of determining whether the person has caused the actuation of a selected sanitizing device associated with the patient and wherein the caution or warning signal is generated unless the person in close proximity or in contact with the patient possesses the monitor and has actuated the selected sanitizing device.

4. A method as described in claim 1 further including the step of causing the monitor to communicate personal identification information relating to the person to the sanitizing device.

5. A method as described in claim 1 wherein the caution or warning signal is generated only if the person is in contact or near contact with the patient or an article worn by or in contact with the patient.

6. A method as described in claim 1 wherein detecting the person in close proximity to or in contact with the patient includes detecting contact or near contact with a patient support apparatus that supports the patient.

7. A method for promoting hygienic practices comprising:
   detecting a person who has come into a patient's room within a first distance of the patient regardless of whether the person possesses a monitor capable of transmitting information;
   detecting the person within a second distance of the patient that is closer to the patient than the first distance and in at least close proximity to the patient regardless of whether the person possesses a monitor capable of transmitting information;
   determining through operation of a processing assembly whether a sanitizing device has been actuated, and
   generating a first selected message if the person has been detected sequentially coming within the first and second distances of the patient and the sanitizing device has not been actuated.

8. A method as described in claim 7 further including causing a second selected message different from the first message to be displayed after detecting the person within the first distance of the patient.

9. A method as described in claim 8 further including the steps of: determining through operation of the processing assembly whether the person possesses a monitor and generating the first selected message if the person does not possess the monitor and is detected in at least close proximity to the patient.

10. A method as described in claim 7 further including the step of detecting the person specifically within a third distance of the patient closer to the patient than the second distance and in contact or near contact with the patient or an article contacting the patient, and generating a warning signal different from the first selected message following detection of the person within the third distance if the sanitizing device has not been actuated prior to such detection.

11. A method as described in claim 7 wherein the first selected message is generated if the sanitizing device has not been actuated within a preselected period of time.

12. A method as described in claim 7 wherein the first selected message is generated if the sanitizing device has not been actuated within the patient's room.

13. A system for promoting hygienic practices, comprising:
   a patient support apparatus;
   a proximity sensor operatively associated with the patient support apparatus, the proximity sensor being specifically responsive to the presence of a person in close proximity to and/or in contact with the patient support apparatus regardless of whether the person possesses a monitor capable of transmitting information, the proximity sensor being capable of generating an electrical signal upon detecting the presence of the person in close proximity and/or in contact with the patient support apparatus, and an indicator device operatively associated with the proximity sensor.

14. A system as described in claim 13 wherein the proximity sensor is a charge transfer sensor specifically responsive to contact or near contact with the patient support apparatus and at least a part of the proximity sensor is mounted to the patient support apparatus.

15. A system as described in claim 13 further including:
means for generating a first signal when the proximity sensor has detected a person in close proximity to and/or in contact with the patient support apparatus;
a sanitizing device; and
a processing assembly for determining whether the sanitizing device has been actuated and causing actuation of the indicator device if the proximity sensor detects the presence of a person in close proximity to and/or in contact with the patient support apparatus and the sanitizing device has not been actuated.

16. A system as described in claim 15 further including a second sensor for detecting the presence of a person who is not proximal to or in contact with the patient support apparatus regardless of whether the person possesses a monitor capable of transmitting information, the processing assembly being capable of determining whether the second sensor and the proximity sensor associated with the patient support apparatus are actuated in sequence as a condition of causing actuation of the indicator device.

17. A system as described in claim 15 further including means for determining whether the person has actuated the sanitizing device, the sanitizing device being associated with the patient support apparatus.

18. A system as described in claim 15 further including means for transmitting personal identity information relating to the person and sanitizing device actuation information to the processing assembly.

19. A system as described in claim 15 further including means for recording a violation of hygiene practices upon actuation of the indicator device.

20. A system for monitoring patients, comprising:
a patient support apparatus;
a room containing the patient support apparatus;
a first detector for detecting whether a person in the room has come within a first selected distance of the patient support apparatus regardless of whether the person possesses a monitor capable of transmitting information;
a second detector for specifically detecting whether the person has come within a second selected distance of the patient support apparatus that is in close proximity to and/or in contact with the patient support apparatus and closer to the patient support apparatus than the first selected distance, the second detector being capable of detecting the person regardless of whether the person possesses a monitor capable of transmitting information;
a sanitizing device;
a processing assembly for determining whether the person has sequentially actuated the first and second detectors and whether the sanitizing device has been actuated, and
an indicator device operatively associated with the processing assembly for generating a first message if the person is detected sequentially by the first detector and then the second detector and the sanitizing device has not been actuated.

21. A system as described in claim 20 wherein the second detector is a proximity sensor capable of specifically detecting whether a person is in contact or near contact with a patient on the patient support apparatus.

22. A system as described in claim 21 wherein the second detector is a charge transfer sensor.

23. A system as described in claim 20 wherein the processing assembly is capable of causing the indicator device to generate a second message when the first detector has detected a person, the first detector being nonresponsive to a person supported by the patient support apparatus.

24. A system as described in claim 20 further including a third detector, the third detector being mounted to the patient support apparatus for detecting only whether the person has come within a third selected distance of the patient support apparatus closer than the second selected distance.

25. A system for monitoring a patient, comprising:
a proximity sensor securable to the patient or an article in contact with the patient, the proximity sensor being specifically responsive to contact or near contact with the patient or the article by another person regardless of whether the other person possesses a monitor capable of transmitting information, the proximity sensor being capable of generating an electrical signal upon such contact or near contact;
an indicator device operatively associated with the proximity sensor.

26. A system as described in claim 25 wherein the proximity sensor includes a charge transfer sensor and a connecting device for securing the charge transfer sensor to the patient such that the patient's body or the article in contact with the patient is incorporated as an electrode portion of the charge transfer sensor.

27. A system as described in claim 25 further including a sanitizing device, and a processing assembly operatively associated with the proximity sensor and the sanitizing device and configured to determine whether the sanitizing device has been used and to cause the actuation of the indicator device if the sanitizing device has not been used prior to the other person contacting or nearly contacting the patient or the article in contact with the patient.

28. A system as described in claim 25 further including a sanitizing device associated with a patient care area and a processing assembly configured to determine whether the sanitizing device associated with the patient care area has been actuated and to cause the indicator device to signal a warning if the sanitizing device associated with the patient care area has not been actuated prior to detection of the other person by the proximity sensor.

29. A system as described in claim 28 further including an image recording device operatively associated with the processing assembly for recording the image of the other person if the sanitizing device has not been actuated prior to the other person's contacting or coming in near contact with the patient or the article in contact with the patient.

30. A system as described in claim 25 further including a room containing the patient, a second proximity sensor for detecting the other person in the room prior to his making contact or near contact with the patient or the article in contact with the patient regardless of whether the other person possesses a monitor capable of transmitting information, a sanitizing device, and a processing assembly configured: 1) to determine the whether the second proximity sensor and the proximity sensor securable to the patient have been actuated, 2) to determine whether the sanitizing device has been operated, 3) to cause a first message to be displayed by the indicator device if the second proximity sensor detects the other person, and 4) to cause a second message to be displayed by the indicator device if the sanitizing device has not been operated in the room prior to the other person contacting or nearly contacting the patient or the article in contact with the patient.

31. A system for promoting hygienic practices, comprising:
    a patient support apparatus;
    a portable monitor capable of storing and transmitting health care worker identification information;
    a proximity sensor operatively associated with the patient support apparatus, the proximity sensor being specifically responsive to the presence of a person in close proximity to and/or in contact with the patient support apparatus regardless of whether the person possesses the portable monitor, the proximity sensor being capable of generating an electrical signal upon detecting the presence of the person in close proximity and/or in contact with the patient support apparatus,
    means for determining whether a person in close proximity to or in contact with the patient support apparatus possesses the portable monitor, and
    an indicator device operatively associated with the proximity sensor.

32. A system for monitoring patients, comprising:
    a patient support apparatus;
    a room containing the patient support apparatus;
    a portable monitor;
    a first detector for detecting whether a person in the room has come within a first selected distance of the patient support apparatus regardless of whether the person possesses the portable monitor;
    a second detector for specifically detecting whether the person has come within a second selected distance of the patient support apparatus that is in close proximity to and/or in contact with the patient support apparatus and closer to the patient support apparatus than the first selected distance, the second detector being capable of detecting the person regardless of whether the person possesses the portable monitor;
    a sanitizing device;
    a processing assembly for determining whether the person has sequentially actuated the first and second detectors and whether the sanitizing device has been actuated, the portable monitor being capable of transmitting information to the processing assembly, and
    an indicator device operatively associated with the processing assembly for generating a first message if: 1) the person is detected sequentially by the first detector and then the second detector and 2) the sanitizing device has not been actuated or the person is not wearing the portable monitor, the processing assembly being further capable of causing the indicator device to generate a selected message if the person has been detected by the first and second detectors and is not wearing the portable monitor.

* * * * *